United States Patent
Martin et al.

(10) Patent No.: US 9,562,874 B2
(45) Date of Patent: Feb. 7, 2017

(54) BIOSENSOR WITH IMPROVED INTERFERENCE CHARACTERISTICS

(71) Applicant: Abbott Point of Care Inc., Princeton, NJ (US)

(72) Inventors: Glenn Martin, Ottawa (CA); G. Bruce Collier, Fitzroy Harbour (CA); Dan Wang, Kanata (CA)

(73) Assignee: Abbott Point of Care Inc., Princeton, NJ (US)

( * ) Notice: Subject to any disclaimer, the term of this patent is extended or adjusted under 35 U.S.C. 154(b) by 499 days.

(21) Appl. No.: 14/206,174

(22) Filed: Mar. 12, 2014

(65) Prior Publication Data

US 2014/0262776 A1 Sep. 18, 2014

Related U.S. Application Data

(60) Provisional application No. 61/787,408, filed on Mar. 15, 2013.

(51) Int. Cl.
*G01N 27/30* (2006.01)
*C12Q 1/00* (2006.01)
*G01N 27/327* (2006.01)

(52) U.S. Cl.
CPC ........... *G01N 27/3271* (2013.01); *C12Q 1/004* (2013.01); *G01N 27/3277* (2013.01); *G01N 2333/90206* (2013.01); *G01N 2333/90683* (2013.01)

(58) Field of Classification Search
CPC ............ G01N 27/3271; G01N 27/3277; G01N 2333/90683; C12Q 1/004
See application file for complete search history.

(56) References Cited

U.S. PATENT DOCUMENTS

| | | |
|---|---|---|
| 4,954,087 A | 9/1990 | Lauks et al. |
| 5,200,051 A | 4/1993 | Cozzette et al. |
| 5,514,253 A | 5/1996 | Davis et al. |
| 5,554,339 A | 9/1996 | Cozzette et al. |
| 5,821,399 A | 10/1998 | Zelin |
| 6,030,827 A | 2/2000 | Davis et al. |
| 7,682,833 B2 | 3/2010 | Miller et al. |
| 7,723,099 B2 | 5/2010 | Miller et al. |
| 8,255,034 B2 | 8/2012 | Heller et al. |
| 2005/0067278 A1* | 3/2005 | Sode ............ C12Q 1/004 204/403.04 |
| 2005/0186652 A1* | 8/2005 | Wong ............ C12Q 1/004 435/25 |
| 2013/0343955 A1 | 12/2013 | Doyle et al. |

OTHER PUBLICATIONS

Anal. Chem, 1974, 46, 1769.

(Continued)

*Primary Examiner* — Susan D Leong
(74) *Attorney, Agent, or Firm* — Kilpatrick Townsend & Stockton LLP

(57) ABSTRACT

This invention relates to mutagenized redox oxidase enzymes used to design enzyme electrodes with improved interference characteristics in the presence of mediator and oxygen in the assay. This recombinant modified enzyme has enhanced capability to transfer electrons to redox mediator instead of its natural electron acceptors such as $O_2$, NAD, NADP, etc., which will improve the assay performance with less interference and higher sensitivity.

20 Claims, 15 Drawing Sheets

(56) References Cited

OTHER PUBLICATIONS

Bartlett, et al., Talanta, 1991,38, 57.
Bartlett, et al., J. Electroanal. Chem., 1987, 224, 37.
Bruno, et al., J. Electrochim. Acta, 1977, 22, 451.
Cass, et al., Anal. Chem. 1984, 56, 667.
Cass, et al., J. Electroanal. Chem. 190, 1985, 117-127.
Durao, et al., 2008, J. Biol. Inorg. Chem., 13: 183-193.
Enguita, et al., 2003, The Journal of Biological Chemistry, 278(21): 19416-19425.
Faulds, et al., J. Chem. Soc. Faraday trans., 1986, 82, 1259.
Guilbault, et al., J. Am. Chem. Soc., 1969, 91, 2164.
Hassan-Abdallah, et al., 2006, Biochemistry, 45: 9454-9462.
J. Am. Chem. Soc., 1991,113, 1394.
Am. Chem. Soc. 1970, 92, 2533.
J. Chem. Soc. Chem. Commun., 1987, 1603.
J. Chem. Soc. Faraday trans., 1992, 88, 2677.
J. Phys. Chem., 1992,96, 3579.
Jorns, et al., 2010, Biochemistry, 49: 3631-3639.
Reiss, et al., 2011, BMC Biotechnology, 11:9.
Shimizu, et al., 1999, 38: 3034-3042.
Shimizu, et al., 2003, J. Biochem.,133: 767-772.
Shleev, et al.,2005, Biosensors and Bioelectronics, 20: 2517-2554.
Solomon, et al., 1996, Chem. Rev. 96: 2563-2605.
Updike, et al., Nature, 1967, 214, 986.
Waller, et al., J. Anal. Chem. 1986, 58, 2979.
Weetall, et al., 1988.
Xu, et al., 2005, Biochemistry and Biotechnology, 35: 283.
Yabuki, et al., J. Chem. Soc. Chem. Commun., 1989, 945.
Youle, et al., 1978, Plant Physiol., 61: 13.
Zeibig, et al., "Renal elimination of troponin T and troponin I", Clinical Chemistry 49, 1191-1193. 2003.
Zhang, et al., 2012, African Journal of Biotechnology, 11(24): 6603-6611.
Zhao & Jorns, 2006, Biochemistry 45: 5985-5992.
Anal. Bioanal. Chem., 3871 18991 2007.
Clark, et al., Phil. Trans. R. Soc. Lond. B 316, 85-94.
Heller, et al., J. Am. Chem. Soc., 1988, 110, 2615.

* cited by examiner

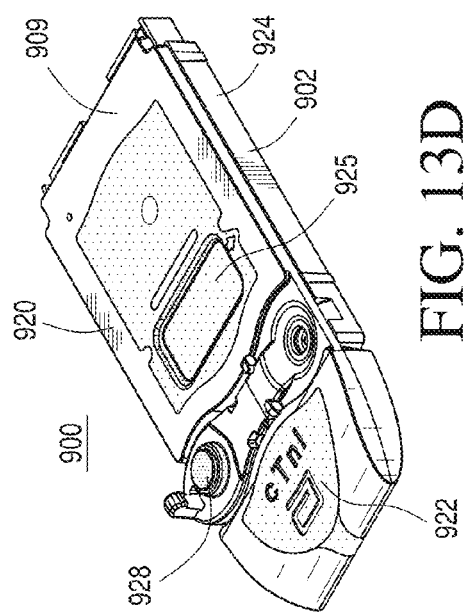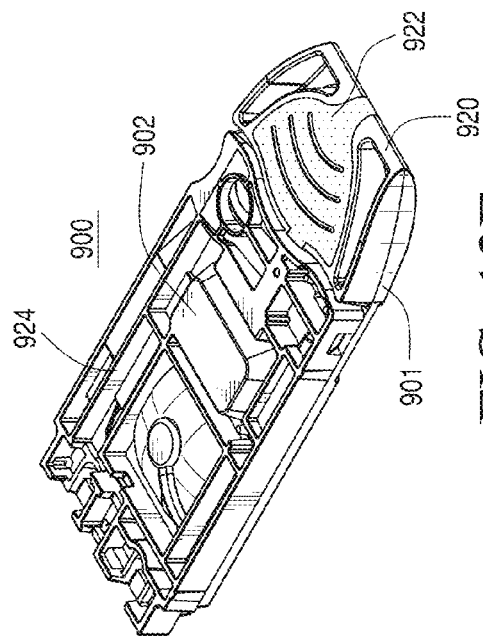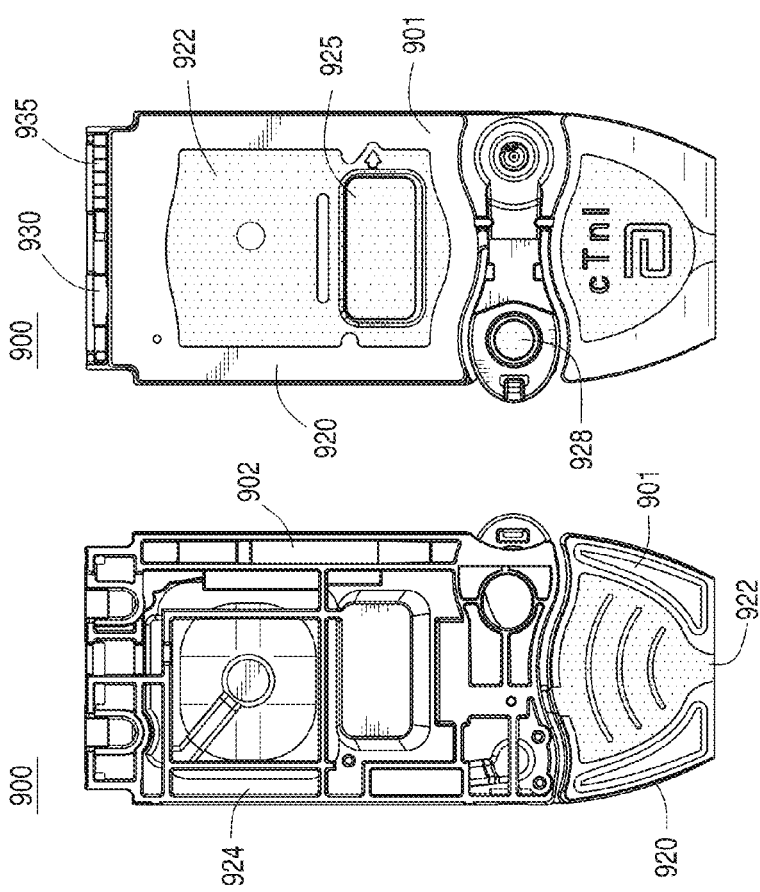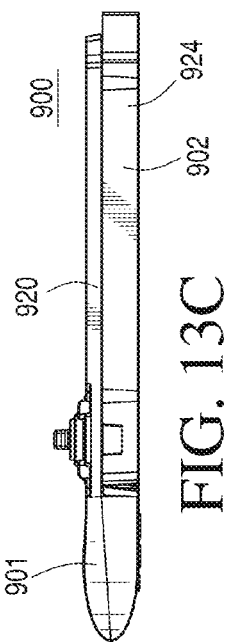

| Sequence ID | Primer Name | Mutation | Mutation Sequence | Amino Acid | Clone ID |
|---|---|---|---|---|---|
| None | None | None Lys wildtype | AAA | Lys265 | BACSOX2 |
| 2 | Wdmps1 | Ala | GCT | Ala265 | SOXFA1-x |
| 3 | Wdmps3 | Met | ATG | Met265 | SOXFM1-x |
| 4 | Wdmps5 | Gln | CAG | Gln265 | SOXFQ1-x |
| 5 | Wdmps7 | Arg | CGT | Arg265 | SOXFR1-x |

FIG. 14

| SOx | $i_{ox}$init | $i_{ox}$5min | ratio |
|---|---|---|---|
| prodT 65kD | 6.2 | 6.8 | 1.1 |
| Wildtype 48kD | 5.6 | 7.3 | 1.3 |
| FM1-3 | 5.2 | 6.2 | 1.2 |
| FA1-4 | 4.5 | 5.0 | 1.1 |
| FR1-4 | 3.7 | 5.6 | 1.5 |
| FQ1-3 | 5.2 | 6.8 | 1.3 |

BIOSENSOR WITH IMPROVED INTERFERENCE CHARACTERISTICS

CROSS-REFERENCE TO RELATED APPLICATIONS

This application claims priority to U.S. Provisional Application No. 61/787,408 filed on Mar. 15, 2013, the entirety of which is hereby incorporated by reference.

SEQUENCE LISTING

This application contains a Sequence Listing which has been submitted in ASCII format via EFS-Web and is hereby incorporated by reference in its entirety. Said ASCII copy, created on Mar. 14, 2013, is named 215105.07100_SL.txt and is 15,335 bytes in size.

FIELD OF THE INVENTION

The present invention relates generally to a modified redox enzyme-mediator biosensor configured to provide decreased interference and, more particularly, to a genetically mutated sarcosine oxidase or bilirubin oxidase enzyme based biosensor engineered with an enhanced ability to transfer electrons to a suitable mediator instead of a natural electron acceptor. The present invention may be used for determining a concentration of creatinine in a sample using a creatinine biosensor that exhibits decreased interference. The present invention may also be used for determining a concentration of bilirubin in a sample using a bilirubin oxidase enzyme.

BACKGROUND OF THE INVENTION

Enzyme electrode based biosensors cover a broad application field, including clinical diagnostics, food analysis and environmental monitoring and control. Since 1962 when the first glucose sensor was developed by Clark and Lyons, over 100 enzyme electrode based biosensor tests have been developed and made commercially available. (Phil. Trans. R. Soc. Lond. B 316, 85-94, 1987). By definition, biosensors are devices comprising an analyte and a selective interface in close proximity or integrated with a transducer, which relays an interaction between the interface and the analyte, directly or through a mediator. The analyte interface is a bioactive substance, e.g., an enzyme, antibody, or microorganism, etc., that is capable of recognizing cognate analytes and configured to regulate the specificity and sensitivity of the device. The transducer converts the biochemical signal into an electrical signal, which can be suitably processed and output.

Electrochemical biosensors are a common class of enzyme electrode based biosensors, and are generally based on the fact that during the bio-interaction process, electrochemical species such as electrons are consumed or generated producing an electrochemical signal that can be measured by an electrochemical detector. An amperometric enzyme electrode is one type of an electrochemical biosensor that has been used widely as it is capable of directly transducing the rate of an enzyme-catalyzed reaction into a current. More specifically, amperometric biosensors function by the production of a current when a potential is applied between two electrodes.

The bioactive substances found in amperometric enzyme electrodes commonly comprise redox enzymes that oxidize substrates by accepting and transferring electrons to electron acceptors (e.g., $O_2$). Amperometric enzyme electrodes are configured to measure a current proportional to the concentration of $O_2$ or the rate of production of the product $H_2O_2$. However, such biosensors may be dependent on the concentration of dissolved $O_2$ in the sample. For example, the rate of electrochemical reduction of $O_2$ depends on the rate of diffusion of oxygen from the bulk solution, which in turn is dependent on the concentration gradient and hence the bulk oxygen concentration. Thus, such biosensors are dependent on the concentration of dissolved oxygen in the bulk solution.

In order to overcome these problems, the concept of using artificial electron acceptors evolved to avoid the reduction of oxygen. In these biosensors, all the substances having conversion potential lower than the electrode potentials contribute to the overall electrochemical signal. The most common example is that at the oxidation potential of +600 mV along with $H_2O_2$ other metabolites such as uric acid, ascorbic acid, glutathione, etc., also get oxidized and interfere with the electrochemical signal. It is therefore, important to apply an electrode potential as low as possible. In order to achieve a low electrode potential, electrochemically active electron acceptors to which the enzyme can donate electrons were investigated. In this context, some artificial electron acceptors having low oxidation potentials were discovered. These artificial electron acceptors are commonly called mediators. This approach leads to a considerable reduction of electrochemical interferences and the development of mediated biosensors. Thus, mediated biosensors can be constructed with the enzymes that can donate electrons to electrochemically active artificial electron acceptors.

Mediated biosensors typically employ a two step procedure in which the enzyme takes part in first a redox reaction with the substrate and is in turn reoxidized by a mediator and finally the mediator is oxidized by the electrode. The amperometric procedure leads to the utilization of a lower redox potential that can be used for $H_2O_2$ detection. If the fixed concentration of an electron acceptor is retained within the enzyme layer, the operational stability of the sensor can be increased. The amperometric biosensors incorporating immobilized mediators therefore provide an effective alternative to peroxide detecting systems.

Mediators are artificial electron transferring agents that can readily participate in the redox reaction with the biological component and thus help in rapid electron transfer. It is a low molecular weight redox couple, which shuttles electrons from the redox center of the enzyme to the surface of the indicator electrode. During the catalytic reaction, the mediator first reacts with the reduced enzyme and then diffuses to the electrode surface to undergo rapid electron transfer. The rate of production of the reduced mediator is measured amperometrically by oxidation at the electrode. Advantageously, mediated enzyme electrodes are known to be less susceptible to interfering substances due to lower electrode potentials.

In 1984, Cass et al. developed a biosensor using a ferrocene mediator for a glucose sensor design (Cass et al., Anal. Chem., 1984, 56, 667), which enabled lower potential detection with less interference. Therefore, choosing suitable mediators is another key component for mediator-enzyme electrode design. The most commonly used mediators are Ferrocyanide or Ferrocene and Quinone deriviatives. Osmium complexes, polypyrrole, organic dyes are also mediators considered under certain circumstances.

The typical mediator-enzyme coupling sensor involves either covalently attaching the mediator to the enzyme or enzyme immobilization. Previous studies have focused on covalently attaching different mediators to the backbone of enzymes to enhance electron transfer directly to the electrode. (Heller et al., J. Am. Chem. Soc., 1988, 110, 2615; J. Am. Chem. Soc., 1991, 113, 1394; J. Phys. Chem., 1992, 96, 3579; Bartlett et al., Talanta, 1991, 38, 57; J. Chem. Soc. Chem. Commun., 1987, 103). However, the studies observed poor stability of the sensor due to mediator decomposition. Different mediator derivatives also play important impacts on the sensor performance. As for immobilized enzymes on the electrode, researchers have tried different materials including hydrogels (Updike et al., Nature, 1967, 214, 986; Guilbault et al., J. Am. Chem. Soc., 1969, 91, 2164; 1970, 92, 2533; Anal. Chem., 1974, 46, 1769), conducting polymers (Foulds et al., J. Chem. Soc. Faraday trans., 1986, 82, 1259; Waller et al., J. Anal. Chem., 1986, 58, 2979; Yabuki et al., J. Chem. Soc. Chem. Commun., 1989, 945; Bartlett et al., J. Electroanal. Chem., 1987, 224, 37; J. Chem. Soc. Faraday trans, 1992, 88, 2677), non-conducting polymers (Burno et al., J. Electrochim. Acta, 1977, 22, 451) and silane modified surfaces (Weetall et al., 1988) in analytical uses of immobilized biological compounds for detection, medical and industrial uses. However, this approach is associated with higher background and interference problems. It also requires efforts on studying and evaluating of different materials for immobilizing or entrapping enzymes on the sensor.

While many native enzymes can be used in electrochemical biosensors using mediators, several enzymes are unable to utilize mediators. Cass et al. investigated 11 different enzymes and suggested that Pyruvate oxidase, Sarcosine oxidase, Oxalate oxidase, Choline oxidase, lipoamide dehydrogenase, alcohol dehydrogenase work at least 10 times less efficiently compared to glucose oxidase using a ferrocinium ion as an electron acceptor. The study notes "glucose oxidase used a variety of electron acceptors," whereas "some (oxidases) were reported to use oxygen specifically." (Cass et al., J. Eletroanal. Chem. 190, 1985, 117-127) making them less useful for mediated electron acceptors. Ramanavicius et al. (Anal. Bioanal. Chem., 387, 1899, 2007) reported that by replacing oxygen with ferrocyanide ions, a creatine sensor was capable of design that exhibited better sensitivity, accuracy and less interference. However, the sensor is sensitive to oxygen concentration in the sample. All the measurements have to be operated in oxygen-free conditions (<5 µM of $O_2$) using native sarcosine oxidase enzyme.

Accordingly, previous research suffered from mediator selection and the oxygen concentration in the sample using native enzymes for enzyme electrode design. The need therefore exists for biosensor designs that provide a reduced oxygen interference and sensitivity for oxidase based sensors.

SUMMARY OF THE INVENTION

In one embodiment, the present invention is directed to a device for detecting a target analyte. The device may include an electrochemical cell, an electron redox mediating molecule, and a recombinant modified enzyme. The a recombinant modified enzyme may be engineered to prevent transfer of electrons to a natural electron acceptor, transfer electrons to the electron redox mediating molecule, and provide enzymatic activity against the target analyte to generate an electrochemical signal dependent on a concentration of the target analyte in a sample.

In some aspects, the natural electron acceptor may be oxygen, nicotinamide adenine dinucleotide (NAD), or nicotinamide adenine dinucleotide phosphate (NADP). In some embodiments, the target analyte may be selected from the group consisting of sarcosine, glucose, lactose, creatinine, creatine, pyruvate, and bilirubin.

In some aspects, the recombinant modified enzyme may include a mutation of a protein coding sequence for a starting enzyme. In some embodiments, the starting enzyme may be sarcosine oxidase and the mutation may be a Lys265 to Arg265 mutation of the starting enzyme. In alternative embodiments, the starting enzyme may be bilirubin oxidase and the mutation may modify an active site of the bilirubin oxidase for oxygen reduction and electron transfer to the natural electron acceptor of bilirubin oxidase located in a trinuclear cluster of bilirubin oxidase.

In another embodiment, the present invention is directed to a device for detecting a target analyte. The device includes an electron redox mediating molecule and a recombinant modified enzyme comprising a mutation of a protein coding sequence for a starting enzyme. The mutation may be engineered to modify an active site of the starting enzyme for oxygen reduction and electron transfer to a natural electron acceptor of the starting enzyme permitting transfer of electrons to the electron redox mediating molecule, and the recombinant modified enzyme maintains enzymatic activity against the target analyte.

In some aspects, the target analyte is selected from the group consisting of sarcosine, glucose, lactose, creatinine, creatine, pyruvate, and bilirubin. In some embodiments, the electron redox mediating molecule may be selected from the group consisting of: ferrocene, ferrocene derivatives, ferrocyanide, quinone derivatives, osmium complexes, ruthenium complexes, transition metal complexes, iron organo complexes, polypyrrole and other conductive polymers, tetracyanoquinodimethane (TCNQ), and methylene blue and other organic dyes.

In another embodiment, the present invention is directed to an electrochemical biosensor. The biosensor may include a silver/silver chloride electrode connected to one end of a circuit, a conductive metal surface connected to another end of the circuit, and an immobilized enzyme layer. The immobilized enzyme layer may include an electron mediator molecule and a recombinant modified enzyme lacking an ability to transfer electrons to a natural electron acceptor and instead transfers electrons to the electron mediator molecule such that the biosensor performs in the presence of oxygen.

In some aspects, the recombinant modified enzyme is based on protein sequence sp-p40859 from *Bacillus* spp. Strain B-0618 and a DNA sequence that is reverse translated to be optimal for expression in *Escherichia coli*.

In some aspects, the recombinant modified enzyme is sub-cloned into pET28b+ and de-repressed to express sarcosine oxidase by addition of indophenol thiogalactopyranoside. In some embodiments, the recombinant modified enzyme is fused with a pET28b+ hexahistidine region ("hexahistidine" disclosed as SEQ ID NO: 34) for metal column purification.

In another embodiment, the present invention is directed to an electrochemical biosensor for target analyte detection. The biosensor may include a silver/silver chloride reference electrode, an electrode specific for the target analyte, an electron redox mediating molecule, an enzyme specific to the target analyte and configured to generate a terminal product, and a recombinant modified enzyme. The a recombinant modified enzyme may be engineered to prevent transfer of electrons to a natural electron acceptor, transfer electrons to the electron redox mediating molecule, and provide enzymatic activity against the target analyte to generate an electrochemical signal dependent on a concentration of the target analyte in a sample comprising the target analyte in a presence of oxygen.

In another embodiment, the present invention is directed to a method for detecting a target analyte in the presence of oxygen. The method includes contacting a sample with a hybrid enzyme and generating a detectable signal related to a detectable product. The hybrid enzyme may be engineered to modify an active site of a starting enzyme for oxygen reduction and electron transfer to a natural electron acceptor of the starting enzyme permitting transfer of electrons to an electron redox mediating molecule, and maintain enzymatic activity against the target analyte to generate the detectable product.

In some aspects, the detectable product is hydrogen peroxide. In some embodiments, the detectable signal may be generated by an electrochemical sensor.

In another embodiment, the present invention is directed to an electron redox mediating molecule and a recombinant modified enzyme comprising a mutation of a protein coding sequence for a starting enzyme. The mutation is preferably engineered to modify an active site of the starting enzyme for oxygen reduction and electron transfer to a natural electron acceptor of the starting enzyme permitting transfer of electrons to the electron redox mediating molecule.

In some aspects, the rate of reduction of the electron redox mediating molecule for the recombinant modified enzyme may be at least 5-fold greater than that of the starting enzyme. In alternative aspects, the rate of reduction of the electron redox mediating molecule for the recombinant modified enzyme may be at least 10-fold greater than that of the starting enzyme.

BRIEF DESCRIPTION OF THE DRAWINGS

The present invention will be better understood in view of the following non-limiting figures, in which:

FIGS. 13A-13E show top, bottom, side, and perspective views of a biosensor cartridge in a closed position in accordance with some aspects of the invention;

FIG. 14 shows information related to the sarcosine oxidase mutants in accordance with some aspects of the invention;

DETAILED DESCRIPTION OF THE INVENTION

Introduction

Figure 1:
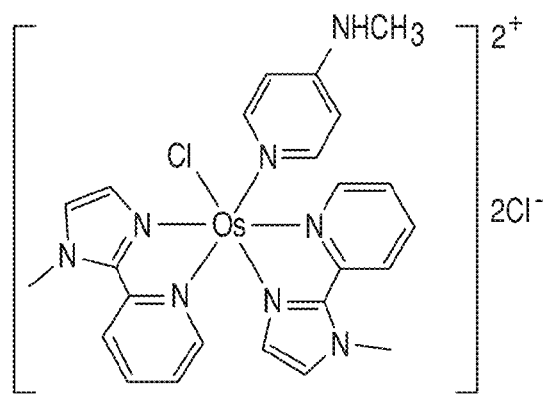
FIG. 1 is a chemical structure of an Osmium redox mediator in accordance with some aspects of the invention.

The present invention is generally applicable to proteins, and more specifically directed to genetically engineered proteins, e.g., enzymes, and the use thereof in qualitative and quantitative assays. More specifically, the present invention relates generally to a modified redox enzyme-mediator biosensor (e.g., a creatinine biosensor) configured to provide decreased interference over traditional redox enzyme-mediator biosensors. The modified redox enzyme-mediator biosensor is configured to provide decreased interference because the biosensor comprises a hybrid enzyme that has been genetically engineered with an enhanced ability to transfer electrons to a suitable mediator instead of a natural electron acceptor (e.g., atmospheric oxygen) of the wild-type enzyme, which typically causes interference problems in traditional biosensors. In some embodiments, the enhanced ability to transfer electrons to a suitable mediator may be conveyed on the wild-type redox enzyme using a mutation that substantially prevents the wild-type redox enzyme from transferring electrons to the natural electron acceptor (e.g., atmospheric oxygen). As such, in accordance with some aspects of the present invention, the qualitative and quantitative assays comprising the hybrid enzyme do not require the removal of oxygen from the sample.

Enzymes of preferably high protein stability and high catalytic activity that are unable to substantially or effectively utilize mediators for purposes of analytical testing may be used as the "starting" enzymes for their modification into hybrid enzymes. The starting enzymes can be natural enzymes, enzymatically-inactive fragments of the natural enzymes, or genetically engineered enzymes. The starting enzymes can be in the form of polypeptides. For example, the starting enzymes may include but are not limited to oxidoreductases, transferases, hydrolases, or lyases. In particular, the starting enzymes may include but are not limited to sarcosine oxidase, bilirubin oxidase, lactate oxidase, pyruvate oxidase, oxalate oxidase, choline oxidase, lipoamide dehydrogenase, alcohol dehydrogenase, or the like.

In some embodiments, the present invention is directed to devices and methods for engineering and using hybrid enzymes for biosensors configured to detect an analyte by their inherent enzymatic reaction, where the analyte is presented in the presence of atmospheric oxygen, typically found in most test samples. The hybrid enzyme may be modified using protein engineering to reduce or eliminate the interference typically observed from atmospheric oxygen. More specifically, a genetically mutated sarcosine oxidase or bilirubin oxidase enzyme based biosensor may be engineered with an enhanced ability to transfer electrons to a suitable mediator instead of a natural electron acceptor (e.g., oxygen, nicotinamide adenine dinucleotide (NAD), or nicotinamide adenine dinucleotide phosphate (NADP)), while the desirable high protein stability and high catalytic activity of the native enzyme has been conserved. Accordingly, for the hybrid enzyme, in one embodiment of this invention, to be suitable for a qualitative or quantitative assay, the hybrid enzyme should meet the following criteria: (1) the mutagenesis should provide an enhanced ability for the hybrid enzyme to transfer electrons to a suitable mediator instead of a natural electron acceptor; and (2) the mutagenesis should not appreciably destroy the enzymatic activity of the resultant hybrid enzyme.

In some embodiments, the hybrid enzyme of the present invention may be a mutant of a wild-type sarcosine oxidase from *Bacillus* spp. B-0618, wherein the mutant sarcosine oxidase has a recombinant modification as compared to the wild-type *Bacillus* spp. B-0618 sarcosine oxidase. In alternative embodiments, the hybrid enzyme of the present invention may be a mutant of a wild-type bilirubin oxidase from *Bacillus pumilus* or *Bacillus subtilis*, wherein the mutant bilirubin oxidase has a recombinant modification as compared to wild-type *Bacillus pumilus* or *Bacillus subtilis* bilirubin oxidase.

More specifically, the wild-type sarcosine oxidase may be mutated at the Lys265 site to be replaced by alanine, glutamine, arginine, or methionine (see, e.g., SEQ ID NO: 7, which provides a wild-type sarcosine oxidase from *Bacillus* spp. B-0618 with Lys265 to Arg265 mutation). In some embodiments, the alanine may be replaced with similar neutral amino acids such as valine, leucine, isoleucine, glycine, serine, threonine, and others. In further embodiments, the wild-type sarcosine oxidase may receive a recombinant modification at Arg49, Thr48, Gly344, Tyr317, Lys348, Arg52, His269, Tyr254, Met245, or Arg52. According to an alternative embodiment, the wild-type sarcosine oxidase gene may be randomly mutated, and an ideal oxidase clone may be selected from a library, having reduced oxygen interference.

In some embodiments, the wild-type bilirubin oxidase produced by *Bacillus pumilis* may receive a recombinant modification or mutagenesis at Met502, Cys492, His419, His497, His493, His153, His107, His105, His422, His491, His424, or His155. According to an alternative embodiment, the wild-type bilirubin oxidase gene may be randomly mutated, and an ideal oxidase clone may be selected from a library, having reduced oxygen interference.

As discussed in further detail herein, the hybrid enzyme may be engineered in some embodiments to be used in qualitative and quantitative diagnostic assay systems. For example, the hybrid enzyme may be implemented in an electrochemical cell to generate a cyclic voltammetry result with an electron mediator chemical to demonstrate a redox signal where electrons are transferred to the mediator species. According to another embodiment, the hybrid enzyme and an electron mediator chemical may be used in a biosensor cartridge to detect an analyte.

The present invention is discussed hereinafter with respect to a mutated or hybrid sarcosine and bilirubin oxidase protein structures with an enhanced ability to transfer electrons to a suitable mediator instead of a natural electron acceptor. However, it should be understood by one skilled in the art that aspects of the present invention may be implemented using any hybrid gene and resultant hybrid protein structure comprising a mutation that provides the hybrid protein structure with the enhanced ability to transfer electrons to a suitable mediator instead of a natural electron acceptor. For example, the hybrid protein structure may be amidohydrolase, amidinohydrolase, and/or sarcosine oxidase when used in the enzymatic cascade to detect creatinine.

Sarcosine Oxidase Mutation

Sarcosine oxidase is an enzyme that catalyzes the oxidative demethylation of sarcosine to yield glycine, $H_2O_2$, and 5,10-$CH_2$-tetrahydrofolate in a reaction requiring $H_4$-tetrahydrofolate and oxygen. Sarcosine oxidase has been identified as an enzyme being unable to effectively utilize mediators in a biosensor and instead uses a natural electron acceptor (e.g., oxygen, NAD, or NADP). Therefore, according to the present invention, sarcosine oxidase has been selected as a possible starting enzyme for modification because of its high protein stability and high catalytic activity, and its inability to substantially utilize mediators.

One example of a genetically engineered protein can be a hybrid enzyme. For example, an amino acid sequence of a starting protein/enzyme (e.g., wild-type sarcosine oxidase) may be mutated or receive a recombinant modification at a target site or random site such that the resulting amino acid sequence comprises a different artificial amino acid sequence as compared to the starting amino acid sequence. For example, a specific target site or amino acid of the starting amino acid sequence (e.g., a specific site such as Lys265) may be replaced with a foreign or substitute amino acid (e.g., alanine, glutamine, arginine, or methionine) in order to create a hybrid enzyme comprising the starting amino acid sequence with the foreign or substitute amino acid replacement.

The target sites for mutations or recombinant modifications in wild-type sarcosine oxidase were predetermined on the basis of sarcosine and oxygen activation sites. Monomeric sarcosine oxidase enzymes have both sarcosine and oxygen activation sites, and both having flavin cofactors. (Zhao & Jorns, 2006, Biochemistry, 2006, 45:5985-92; Hassan-Abdallah et al., 2006, Biochemistry, 45: 9454-62, Jorns et al. 2010, Biochemistry, 49:3631-9). In exploring potential mutations to use in conjunction with an electron mediator species, these sites proved useful as early exploration target sites. For example, Jorns et al., 2010 performed mutagenesis studies implicating Lys265 as a key interacting species at the oxygen activation site. Accordingly, in some embodiments, the criterion for the selection of a given amino acid as a target mutagenic site was the amino acid's proximity to the oxygen activation site or active site of the enzyme molecule.

Expanding from this criterion for the selection of a given amino acid as a target mutagenic site, several amino acid residues (e.g., an amino acid molecule that has lost a water molecule by becoming joined to a molecule of another amino acid) that can potentially interact with the oxygen activation flavin adenine dinucleotide (FAD) molecule were explored including Arg49 and Thr48. The use of one of these mutations in conjunction with an electron mediator species may allow electron transfer in an electrochemical cell. Even further expanding from this criterion for the selection of a given amino acid as a target mutagenic site, the sarcosine activation site forms an enzyme-FAD-sarcosine intermediate, which may be enzymatically converted to its products with the transfer of electrons. Therefore, a mutation of the sarcosine activation site may be capable of transferring electrons to an electron mediator species. For example, sarcosine activation site mutations may comprise the mutations Gly344, Tyr317, Lys348, Arg52, His269, Tyr254, Met245, and Arg52. More specifically, a mutation of greater than 4 Å from the FAD dioxygen activation site and at an angle of less than 40°, when using the FAD N5 and O4 residues to calculate the angle, may provide a mutation of the oxygen activation site of FAD such that the resultant hybrid enzyme is capable of transferring electrons to an electron mediator species.

In additional or alternative embodiments, the wild-type sarcosine oxidase gene may be randomly mutated, and an ideal oxidase clone may be selected from a library, having reduced oxygen interference. For example, random amino acid changes may be accomplished by inserting a codon sequence NNN into the DNA sequence the wild-type sarcosine oxidase, where N is any of four nucleotides. One constructed mutant may carry point mutations, i.e., amino acid changes, which may result in modification of the synthetic oligonucleotides used for gene synthesis to accomplish reduced oxygen interference.

To produce the mutation or recombinant modification at one or more target sites in the enzyme, an appropriate codon sequence encoding, for example, a replacement amino acid may be inserted into the gene (SEQ ID NO: 1) reverse translated from the protein sequence sp-p40859 from the *Bacillus* spp. Strain B-0618. Once the initial set of suitably mutated DNA molecules is obtained, protein design strategies may be used to express the hybrid enzyme in host cells (e.g., BL21(DE3) *Escherichia coli*). For example, in some embodiments, construction of the hybrid enzyme may comprise synthesizing and assembling synthetic oligonucleotides for sarcosine oxidase that contain the mutations. The synthetic oligonucleotides may then be annealed, assembled, and ligated into an expression vector appropriately restriction digested to accept the assembled oligonucleotide sequence. In another embodiment, construction of the genetically engineered enzyme may comprise in vitro mutagenesis, where mutagenic synthetic oligonucleotides may be designed to have the specific mutations flanked by the wild-type sequence. In accordance with one aspect of the invention, a high fidelity DNA polymerase may be used in concert with 5'-phosphorylated oligonucleotides to generate an amplicon with a specific mutation at the designed site, which is then ligated and transformed into a host for replication and expression.

Accordingly, in some embodiments, the present invention is directed to a biosensor comprising a genetically engineered hybrid oxidase enzyme. The hybrid oxidase enzyme may have at least one amino acid site mutation as compared to a corresponding wild-type oxidase enzyme, and the hybrid oxidase enzyme may be engineered to exhibit improved electron transfer to at least one suitable electron mediator species. The starting wild-type oxidase enzyme should be capable of converting a cognate target analyte or molecule (e.g., N-methylglycine or sarcosine, in the instance that the starting enzyme is sarcosine oxidase (EC 1.5.3.1)) into at least one detectable product (e.g., hydrogen peroxide).

Figure 2:
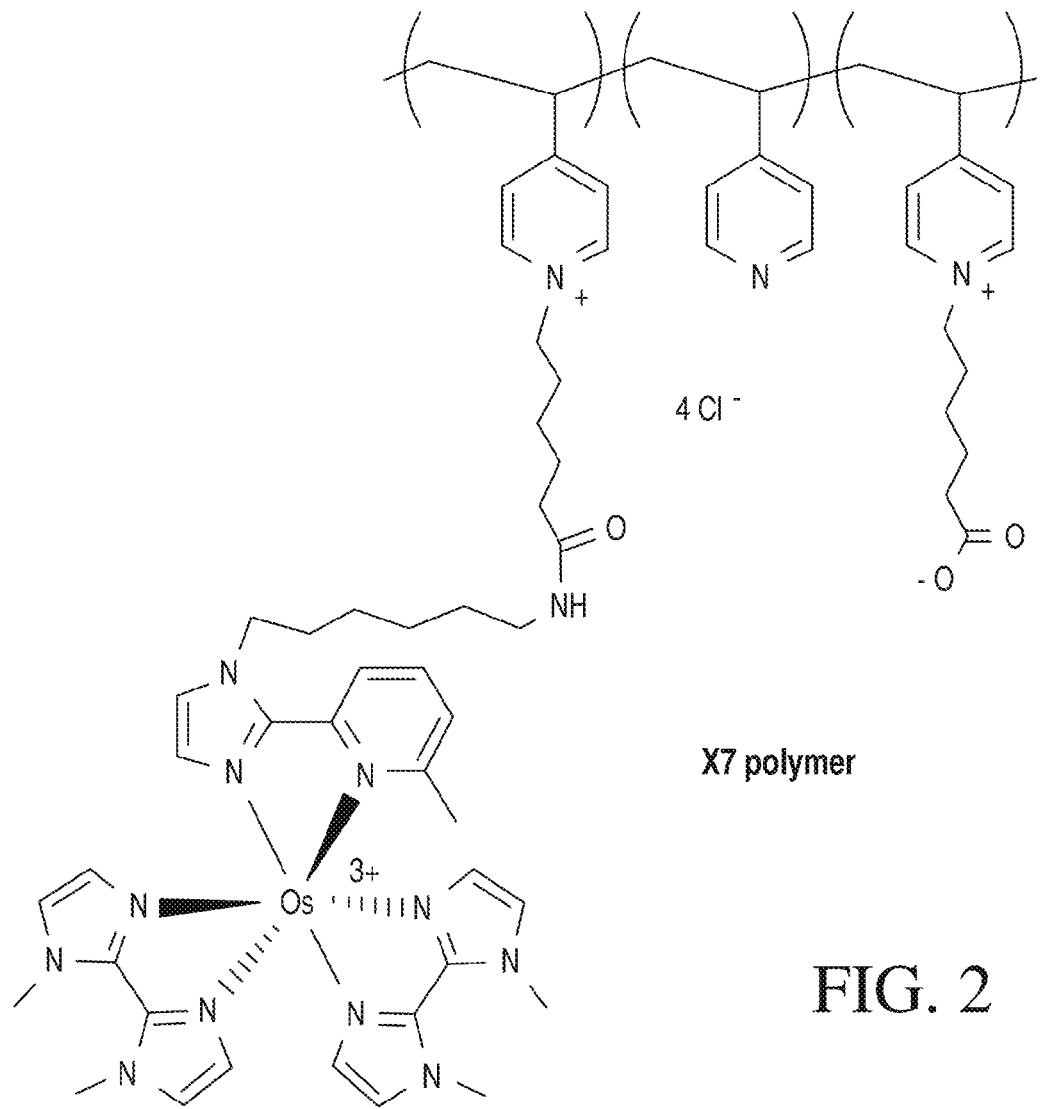
FIG. 2 is a chemical structure of X7 Osmium redox polymer in accordance with some aspects of the invention.

The at least one suitable electron mediator species may be selected based on the following criteria: (i) the mediator should be able to react rapidly with the reduced hybrid enzyme, (ii) the mediator should exhibit reversible heterogeneous kinetics, (iii) the overpotential for the regeneration of the oxidized mediator should be low and not pH dependent, (iv) the mediator should have stable oxidized and reduced forms, and (v) the reduced form should not react with oxygen. For example, the at least one suitable electron mediator species may be ferrocene, ferrocene derivatives, ferrocyanide, quinone derivatives, osmium complexes, ruthenium complexes, transition metal complexes, iron organo complexes, polypyrrole and other conductive polymers, tetracyanoquinodimethane (TCNQ), or methylene blue and other organic dyes. FIG. 1 depicts the chemical structure for an osmium redox mediator and FIG. 2 depicts the chemical structure of X7 osmium redox polymer (see, e.g., U.S. Pat. No. 8,255,034, which is incorporated herein in its entirety by reference), which may be implemented into some aspects of the present invention as a suitable electron mediator species.

In some embodiments, depending upon the assay conditions, a second order rate constant for the mutants (i.e., the rate of reduction of the mediator) has been increased 4-10 fold over that exhibited by the native enzyme. The enhanced rate of reduction of the mediator has been accomplished through a combination of molecular modeling, genetic engineering, and site-directed mutagenesis.

Bilirubin Oxidase Mutation

Bilirubin oxidase is an enzyme that catalyzes the oxidation of bilirubin to yield biliverdin and $H_2O$ in a reaction that requires oxygen. Bilirubin oxidase is known as a blue multi-copper oxidase having four copper ions involved in the enzymatic conversion of bilirubin to biliverdin and the reduction of dioxygen to water. Several other blue multi-copper oxidases are known which also reduce dioxygen to water (reviewed in Solomon et al., 1996, Chem. Rev, 96:2563-2605). There are three types of copper ion sites within these proteins, classified as Type I, II and III. The Type I sites generate a distinct blue color.

Bilirubin oxidase has one type I copper site, one Type II copper site and two Type III copper sites. The type I site is involved in the enzymatic conversion of bilirubin to biliverdin. Whereas, the Type II and Type III copper sites are closely associated with each other and are known as the trinuclear cluster (TNC). The TNC site is the location of dioxygen reduction (Shleev et al., 2005, Biosensors and Bioelectronics, 20: 2517-2554). Mutation of the Type I copper site of bilirubin oxidase affects enzymatic activity (Shimizu et al., 1999, 38:3034-3042). Shimizu et al. (2003, J. Biochem., 133:767-72) have also mutated many of the key sites involved in the Type III copper involved in the reduction of dioxygen. However, none of these references attempted to couple the loss of recombinant enzymatic activity of dioxygen reduction to an electron mediator species, which is described in the present invention.

The *Bacillus subtilis* 65 KDa bacterial endospore coat protein (cotA) exhibits a laccase activity (Enguita et al., 2003, The Journal of Biological Chemistry, 278(21):19416-425). Zhang et al., 2012, African Journal of Biotechnology, 11(24):6603-11, have cloned and expressed *Bacillus subtillus* cotA in BL21(DE3) *E. coli* and characterized the decolorizing capability of the enzyme. Durao et al., 2008, J. Biol. Inorg. Chem. 13:183-193, have also cloned and expressed *Bacillus subtilis* cotA laccase in a similar system and studied the ability of copper to be incorporated into the enzyme. However, there has been no investigation of using cotA as a bilirubin oxidase enzyme for use in a medical diagnostic assay (Reiss et al., 2011, BMC Biotechnology, 11:9).

One example of a genetically engineered protein can be a hybrid enzyme. For example, an amino acid sequence of a starting protein/enzyme (e.g., wild-type bilirubin oxidase comprising cotA) may be mutated or receive a recombinant modification at a target site or random site such that the resulting amino acid sequence comprises a different artificial amino acid sequence as compared to the starting amino acid sequence. For example, a specific target site or amino acid of the starting amino acid sequence (e.g., a specific site such as Met502) may be replaced with a foreign or substitute amino acid in order to create a hybrid enzyme comprising the starting amino acid sequence with the foreign or substitute amino acid replacement.

The target sites for mutations or recombinant modifications in wild-type bilirubin oxidase were predetermined on the basis of bilirubin and oxygen activation sites. More specifically, in exploring potential mutations to use in conjunction with an electron mediator species, the active site for oxygen reduction and electron transfer to its natural dioxygen substrate located in the TNC consisting of the Type II and Type III copper active sites proved useful as early exploration target sites. Accordingly, in some embodiments, the criterion for the selection of a given amino acid as a target mutagenic site was the amino acid's proximity to the oxygen activation site or active site of the enzyme molecule. Expanding from this criterion for the selection of a given amino acid as a target mutagenic site, the mutagenic sites from *Bacillus pumilis* (based on *Bacillus subtilis*) bilirubin oxidase (cotA BOX) comprising Met502, Cys492, His419, His497, His493, His153, His107, His105, His422, His491, His424, His155 (SEQ ID NO: 8) were explored and exhibited potential for use in conjunction with an electron mediator species (e.g., see Enguita et al., 2003, The Journal of Biological Chemistry, 278(21):19416-425). Alternatively, the mutagenic sites from *Myrrothecium verrucaria* bilirubin oxidase (Mve BOX) comprising His 462, His 398, Met467, Cys457, His456, His458, His136, His134, His96, His403, His94, His401 (SEQ ID NO: 9) were also explored and exhibited potential for use in conjunction with an electron mediator species (e.g., see Shimizu et al., 2003, J. Biochem., 133:767-72).

In additional or alternative embodiments, the wild-type bilirubin oxidase gene may be randomly mutated, and an ideal oxidase clone may be selected from a library, having reduced oxygen interference. For example, random amino acid changes may be accomplished by inserting a codon sequence NNN into the DNA sequence the wild-type bilirubin oxidase, where N is any of four nucleotides. One constructed mutant may carry point mutations, i.e., amino acid changes, which may result in modification of the synthetic oligonucleotides used for gene synthesis to accomplish reduced oxygen interference.

To produce the mutation or recombinant modification at one or more target sites in the enzyme, an appropriate codon sequence encoding for example a replacement amino acid may be inserted into the gene reverse translated from the protein sequence from, for example, the *Bacillus pumilus* spore coat protein gi-194015788 (ZP_03054403). Once the initial set of suitably mutated DNA molecules is obtained, protein design strategies may be used to produce the hybrid enzyme. For example, in some embodiments, construction of the hybrid enzyme may comprise synthesizing and assembling synthetic oligonucleotides for bilirubin oxidase that contain the mutations. The synthetic oligonucleotides may then be annealed, assembled, and ligated into an expression vector appropriately restriction digested to accept the assembled oligonucleotide sequence. In another embodiment, construction of the genetically engineered enzyme may comprise in vitro mutagenesis, where mutagenic synthetic oligonucleotides may be designed to have the specific mutations flanked by the wild-type sequence. In accordance with one aspect of the invention, a high fidelity DNA polymerase may be used in concert with 5'-phosphorylated oligonucleotides to generate an amplicon with a specific mutation at the designed site, which is then ligated and transformed into a host for replication and expression.

Accordingly, in some embodiments, the present invention is directed to a biosensor comprising a genetically engineered hybrid oxidase enzyme. The hybrid oxidase enzyme may have at least one amino acid site mutation as compared to a corresponding wild-type oxidase enzyme, and the hybrid oxidase enzyme may be engineered to exhibit improved electron transfer to at least one suitable electron mediator species. The starting wild-type oxidase enzyme should be capable of converting a cognate target analyte or molecule (e.g., bilirubin, in the instance that the starting enzyme is bilirubin oxidase (EC 1.3.3.5)) into at least one detectable product.

The at least one suitable electron mediator species may be selected based on the following criteria: (i) the mediator should be able to react rapidly with the reduced hybrid enzyme, (ii) the mediator should exhibit reversible heterogeneous kinetics, (iii) the overpotential for the regeneration of the oxidized mediator should be low and not pH dependent, (iv) the mediator should have stable oxidized and reduced forms, and (v) the reduced form should not react with oxygen. For example, the at least one suitable electron mediator species may be ferrocene, ferrocene derivatives, ferrocyanide, quinone derivatives, osmium complexes, ruthenium complexes, transition metal complexes, iron organo complexes, polypyrrole and other conductive polymers, tetracyanoquinodimethane (TCNQ), and methylene blue and other organic dyes.

In some embodiments, depending upon the assay conditions, a second order rate constant for the mutants (i.e., the rate of reduction of the mediator) has been increased 4-10 fold over that exhibited by the native enzyme. The enhanced rate of reduction of the mediator has been accomplished through a combination of molecular modeling, genetic engineering, and site-directed mutagenesis.

Amperometric Electrochemical System for the Detection of a Target Analyte

Figure 3:
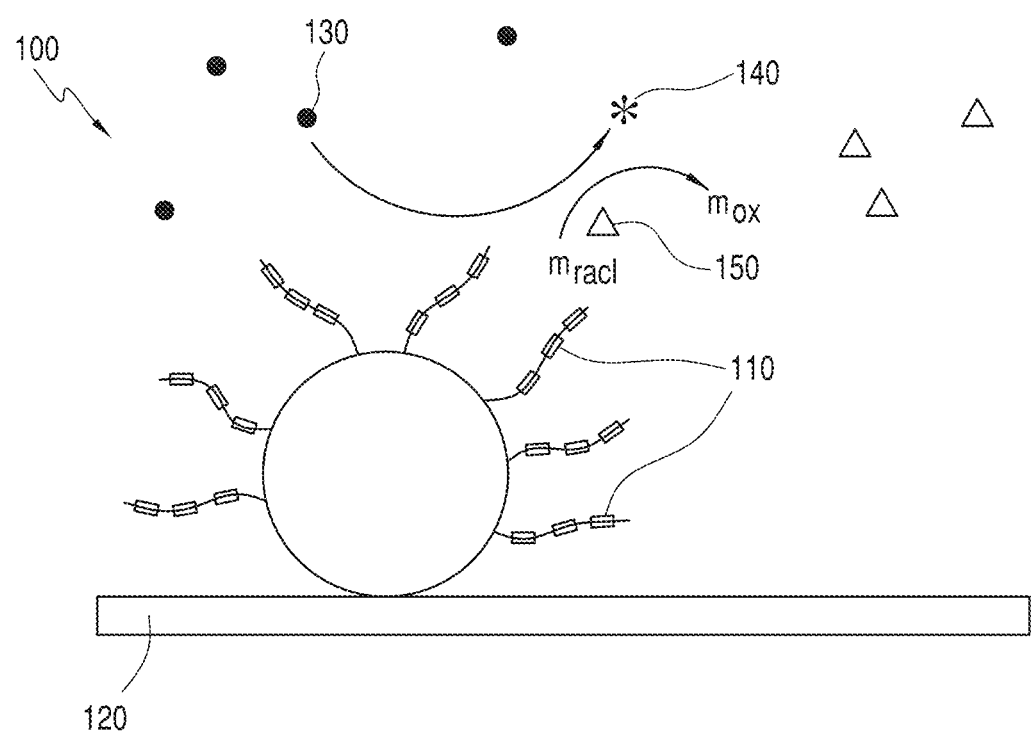
FIG. 3 illustrates the principle of an amperometric electrochemical system in accordance with some aspects of the invention.

FIG. 3 illustrates the principle of an amperometric electrochemical system 100 according to exemplary embodiments of the present invention for determination of the presence and/or concentration of a target analyte, e.g., creatinine or bilirubin. However, it should be understood that while specific embodiments are described for a creatinine or bilirubin assay, the sensor structure and microparticle reagents described herein may also be useful for detecting sarcosine, glucose, lactose, creatine, or pyruvate, among other analytes.

In a contacting step, a sample, e.g., whole blood, plasma, serum, buccal swab, urine, interstitial fluid, cerebrospinal fluid, semen, vaginal swab, nasal swab, tears, environmental sample, or industrial test sample, may be introduced into a conduit or sample holding chamber of a cartridge of the present invention (e.g., a cartridge as disclosed in U.S. Pat. No. 7,723,099, which is incorporated herein by reference in its entirety) with a fluidics format suitable for an assay. The sample may be moved from the conduit or sample holding chamber into contact with a hybrid protein structure or enzyme 110 as describe herein engineered to exhibit improved electron transfer to at least one suitable electron mediator species.

Figure 4:
FIG. 4 shows an X-ray crystallograph depiction of a wild-type bilirubin oxidase protein sequence in accordance with some aspects of the invention.

In some embodiments, the hybrid protein structure or enzyme 110 may be attached on, or close to, at least one amperometric working electrode 120. Accordingly, the at least one amperometric working electrode 120 may be coated with a biolayer comprising a covalently attached hybrid protein structure or enzyme 110. The hybrid protein structure or enzyme 110 is thus immobilized on or in close proximity to the at least one amperometric working electrode 120. The hybrid protein structure or enzyme is depicted in the figures as a linear species; however, it should be understood by those of skill in the art that in reality the hybrid protein structure or enzyme comprises a 3D folded structure, for example as depicted in FIG. 4, (which illustrates the 3D folded structure of Bilirubin Oxidase (BOX)).

A catalytic region on the at least one amperometric working electrode 120 may be defined by a hydrophobic ring of polyimide or another photolithographically produced layer. A microdroplet or several microdroplets (approximately 5-40 nanoliters in size) containing the hybrid protein structure or enzyme in a substantially inactive form, for example bound to latex microparticles, may be dispensed on the surface of each sensor. The photodefined ring contains this aqueous droplet allowing the hybrid protein structure or enzyme coated region to be localized to a precision of a few microns. The catalytic region may be made from about 0.03-2 mm$^2$ in size. The upper end of this size (e.g., 2 mm$^2$) may be limited by a size of a sensor conduit comprising the sensors in present embodiments, and is not a limitation of the invention.

In the contacting step, any target analyte or cognate composition of matter 130 within the sample may be introduced to the hybrid protein structure or enzyme 110 and the at least one amperometric working electrode 120 such that the hybrid protein structure or enzyme 110 may convert the target analyte or cognate composition of matter 130 to a detectable product 140 (e.g., catalyze the conversion of sarcosine to detectable hydrogen peroxide). In some embodiments, the contacting step comprises the introduction of at least one suitable electron mediator species 150 into the reaction between the hybrid protein structure or enzyme 110 and the target analyte or cognate composition of matter 130 such that the at least one suitable electron mediator species 150 may act as an electron acceptor in the catalyzed reaction between the hybrid protein structure or enzyme 110 and the target analyte or cognate composition of matter 130.

As should be understood, the use of the hybrid protein structure or enzyme 110 should improve electron transfer to the at least one suitable electron mediator species 150 over that of the wild-type protein structure. Therefore, the catalytic activity of the hybrid protein structure or enzyme 110 may be more indicative to a concentration or presence of the target analyte within the sample due to the decrease in interference potentially caused by electron transfer to the natural electron acceptors of the wild-type protein structure. For example, the detectable product 140 may cause an electrical potential to be generated across the at least one amperometric working electrode 120 that in turn generates a signal relative to the electrical potential caused by the detectable product 140. As should be understood, the combination of the hybrid protein structure or enzyme 110 and the at least one suitable electron mediator species 150 allows for a lower potential detection with less interference.

In some embodiments, the contacting step may comprise additional steps such as the addition of additional enzymes and/or substrates. For example, an amperometric biosensor for creatinine may be based on a multi-enzyme method, where at least one of the enzymes is a hybrid enzyme. This may involve a three-stage conversion of creatinine to creatine (e.g., using the enzyme creatinine amidohydrolase), creatine to sarcosine (e.g., using the enzyme creatinine amidinohydrolase), and sarcosine to glycine (e.g., using the hybrid enzyme comprising a mutation of the wild-type sarcosine oxidase). In the final stage, consumption of electrochemically detectable oxygen and liberation of hydrogen peroxide ($H_2O_2$) occurs.

Biosensor Comprising Amperometric Working Electrode

Figure 5:
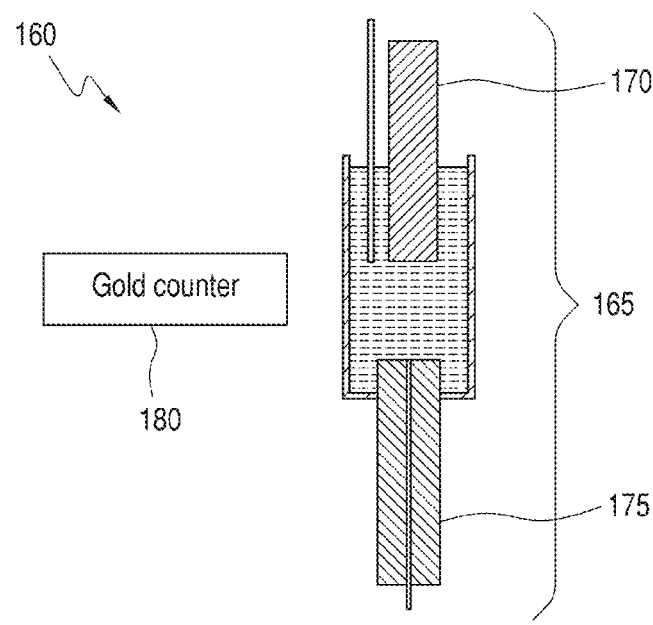
FIG. 5 shows a schematic diagram of electrochemical cell is accordance with some aspects of the invention.

A preferred embodiment of a biosensor 160 comprising: (i) an electrochemical cell 165 including a reference electrode 170 and a working or analyte specific electrode 175, and (ii) a counter electrode 180 is shown in FIG. 5. In some embodiments, the reference electrode 170 may be a silver/silver chloride electrode. In some embodiments, the working electrode 175 may comprise a metal surface including gold, silver, platinum, graphite, carbon, glassy carbon, carbon ink, graphene, or combinations thereof.

Figure 6:
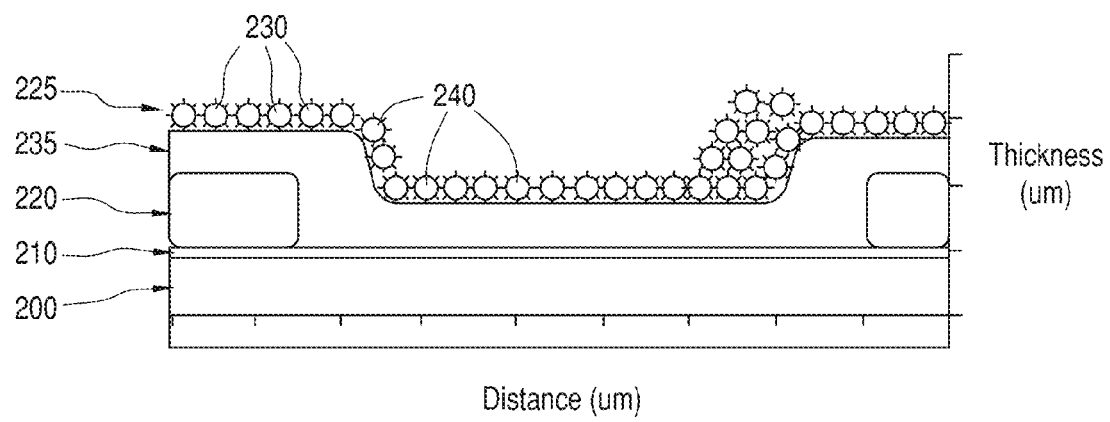
FIG. 6 shows a microfabricated sensor array comprising at least one amperometric working electrode in accordance with some aspects of the invention.

A preferred embodiment of a microfabricated biosensor comprising at least one amperometric working electrode is shown in FIG. 6. In this embodiment, the microfabricated sensor array comprises at least a pair of electrodes comprising a working sensor or electrode and a reference sensor or electrode. For example, the biosensors or electrodes may be fabricated as adjacent structures, respectively, on a support such as a silicon chip.

The electrodes may be formed on a silicon support 200 having a conducting layer or metal surface 210 (e.g., gold) coated with a photodefined layer of polyimide 220. For example, wafer-level microfabrication of a preferred embodiment of the sensor array may be achieved as follows. A planar non-conducting substrate 200 may be used as a base for the sensor array. A conducting layer 210 may be deposited on the substrate 200 by conventional means or microfabrication known to those of skill in the art to form at least one electrode. The conducting layer 210 may comprise a noble metal such as gold or platinum, although other unreactive metals such as iridium may also be used, as many non-metallic electrodes of graphite, conductive polymer, or other materials may also be used.

For example, a base electrode may comprise a square array of 5-10 µm gold disks, e.g., 7 µm gold disks, on 15 µm centers. The array may cover a region, e.g., a circular region, approximately 300 to 900 µm in diameter, optionally 600 µm in diameter, and may be formed by photo-patterning a thin layer of the polyimide of thickness 0.35 µm over a substrate made from a series of layers comprising Si, $SiO_2$, TiW, and/or Au, or combinations thereof. The array of microelectrodes affords high collection efficiency of electroactive species with a reduced contribution from any electrochemical background current associated with the capacitance of the exposed metal. In particular, regularly spaced openings in the insulating polyimide layer define a grid of small gold electrodes at which the p-aminophenol may be oxidized in a 2 electron per molecule reaction.

Microfabrication techniques (e.g. photolithography and plasma deposition) may be utilized for construction of the multilayered sensor structures in confined spaces. For example, methods for microfabrication of the electrochemical biosensors on silicon substrates are disclosed in U.S. Pat. No. 5,200,051, which is hereby incorporated by reference in its entirety. These include dispensing methods, methods for attaching biological reagent, e.g., hybrid enzymes, to surfaces including photoformed layers and microparticle latexes, and methods for performing electrochemical assays.

The microfabricated sensor array may also comprise an electrical connection (not shown) and a biolayer 225 (as discussed above with respect to FIG. 1), which are deposited onto at least a portion of the conducting layer 210 and/or the non-conducting substrate 200. In the present invention, the biolayer 225 may include a porous layer comprising a surface with a sufficient amount of a molecule 230 (e.g., the immobilized hybrid enzyme) may respond to the presence of a target analyte or cognate molecule by producing a change that is capable of measurement.

Optionally, a permselective screening layer 235 may be interposed between the conducting layer 210 and the biolayer 225 to screen electrochemical interferents as described in U.S. Pat. No. 5,200,051, which is hereby incorporated by reference in its entirety. In particular, the electrodes described herein may be manufactured to optimize a signal-to-noise ratio, or amperometric background signal. For example, an intervening polyvinyl alcohol (PVA) layer of about 0.5-5.0 µm thickness (preferably 0.6-1.0 µm) may be placed between the electrodes and the biolayer or hybrid enzyme reagent layer significantly attenuating the background component, as described in U.S. Pat. No. 7,723,099, which is hereby incorporated by reference in its entirety. An advantage of PVA as the background-reducing layer is that noise is reduced without appreciably affecting the Faradaic component of the signal. While the PVA layer reduces the diffusion coefficient of small molecules by about 50% it has been found that it does not change the current at the coated electrodes, for two reasons. First, with PVA layers of about 1 micron thickness, the detected electroactive species is present in a diffusion layer of at least ten times that thickness, so there is little decrease in transport due to the PVA layer. Second, a steady-state current is measured in the biosensor, which is effectively independent of the transport rate and electrode kinetics, but is a function of the enzymatic rate of production of the detectable species, such as hydrogen peroxide generated from sarcosine by the enzyme sarcosine oxidase.

The porous PVA layer may be prepared by spin-coating an aqueous mixture of PVA plus a stilbizonium photoactive, cross-linking agent over the microelectrodes on the wafer. The spin-coating mixture optionally includes bovine serum albumin (BSA). The spin-coating mixture may then be photo-patterned to cover only a region above and around the sensor arrays, and preferably has a thickness of about 0.6 µm.

In specific embodiments, the biolayer 225 may be formed from polystyrene or latex beads 245 of specific diameter in the range of about 0.01 to 5.0 µm. The beads may be modified by covalent attachment of any suitable molecule consistent with the above definition of the biolayer (as discussed in further detail below). Many methods of attachment exist in the art, including providing amine reactive N-hydroxysuccinimide ester groups for the facile coupling of lysine or N-terminal amine groups of proteins. In specific embodiments, the microparticle 240 may be coated with nickel and use a hexahistidine tag (SEQ ID NO: 34) on the molecule to bind the hybrid enzyme.

In one embodiment, the biolayer 225 comprising microparticle beads 240 having surfaces that are covalently modified by a suitable molecule, may be affixed to the sensors by the following method. A microdispensing needle may be used to deposit onto a surface of the electrode or a photo-patterned PVA permselective layer covering the electrode a small droplet of the microparticle reagents. Specifically, in order to bind the microparticle reagents to the electrode, a droplet of about 0.4 nL comprising about 1% solids (i.e., the microparticles) in 0.08% Tween 20 may be microdispensed (e.g., using the method and apparatus of U.S. Pat. No. 5,554,339, which is incorporated herein by reference in its entirety) onto a surface of the electrode or a photo-patterned PVA permselective layer covering the electrode. The droplet may then be allowed to dry. The adherence of the dried microparticles particles to the porous layer substantially prevents dissolution of the microparticles into the sample (e.g., the blood sample). However, in some embodiments additional coupling chemistry may be used to ensure bead immobilization on the porous layer and/or the biosensors. Such techniques are well known in the art.

Microparticle Reagent Fabrication

In some embodiments, microparticles (e.g., carboxylate-modified latex microparticles supplied by Bangs Laboratories Inc. or Seradyn Microparticles Inc.) coated with hybrid enzymes may be prepared for use in detecting target analytes such as thrombin in accordance with some aspects of the present invention. For example, the microparticles may first be buffer exchanged by centrifugation, and then the hybrid enzymes may be added to the microparticles (e.g., the hybrid enzymes may be allowed to passively adsorb onto the microparticles). Inactive groups (e.g., carboxyl groups) on the microparticles may then be activated to form amide bonds to the hybrid enzymes. Microparticle aggregates may then be removed by centrifugation and the finished microparticles may be stored frozen for future use with the systems and devices of the present invention.

System Comprising a Sensor Array Configured for Target Analyte Detection

Figure 7:
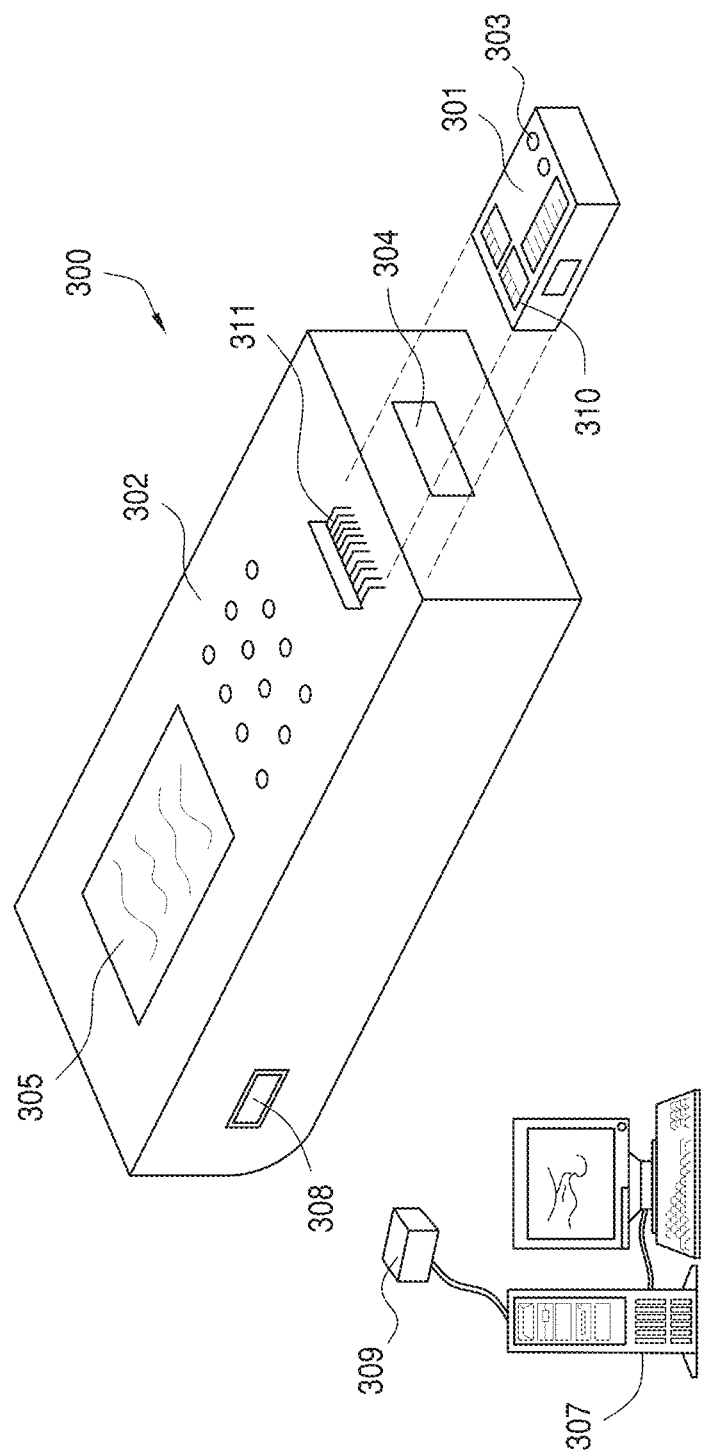
FIG. 7 shows an isometric view of a disposable sensing device and reader device in accordance with some aspects of the invention.

Referring to FIG. 7, the system 300 of the present invention may comprise a self-contained disposable sensing device or cartridge 301 and a reader device or instrument 302. A fluid sample (e.g., whole blood or urine) to be measured is drawn into a sample entry orifice or port 303 in the cartridge 301, and the cartridge 301 may be inserted into the reader device 302 through a slotted opening 304. The reader device 302 may comprise a processor configured to perform measurements of analyte concentration within the fluid sample, as discussed herein in further detail. Measurements and determinations performed by the reader may be output to a display 305 or other output device, such as a printer or data management system 307 via a port on the reader 308 to a computer port 309. Transmission can be via Wifi, Bluetooth link, infrared and the like. Note that where the sensors are based on electrochemical principles of operation, the sensors 310 (e.g., a primary sensor and optionally a reference sensor) in the cartridge 301 make electrical contact with the instrument 302 via an electrical connector 311. For example, the connector may be of the design disclosed in jointly owned U.S. Pat. No. 4,954,087, incorporated herein by reference in its entirety. The instrument 302 may also include a method for automatic fluid flow compensation in the cartridge 301, as disclosed in jointly owned U.S. Pat. No. 5,821,399, which also is incorporated herein by reference in its entirety.

Figure 8:
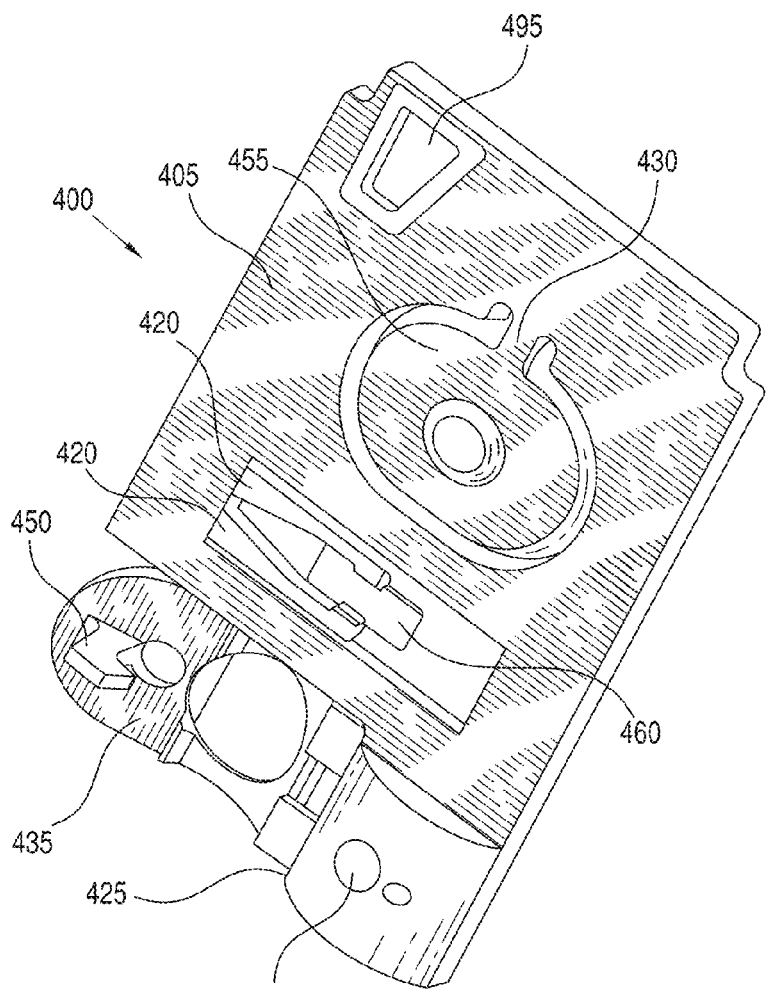
FIG. 8 shows an isometric top view of a biosensor cartridge cover in accordance with some aspects of the invention.
Figure 9:
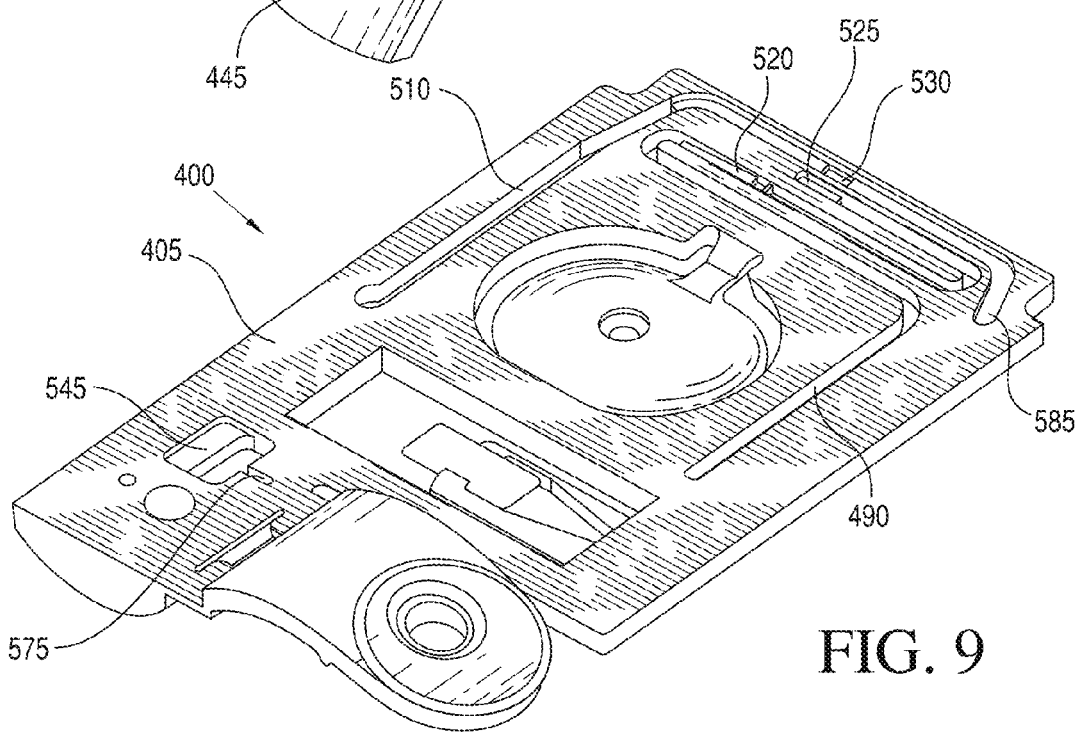
FIG. 9 shows an isometric bottom view of a biosensor cartridge cover in accordance with some aspects of the invention.
Figure 10:
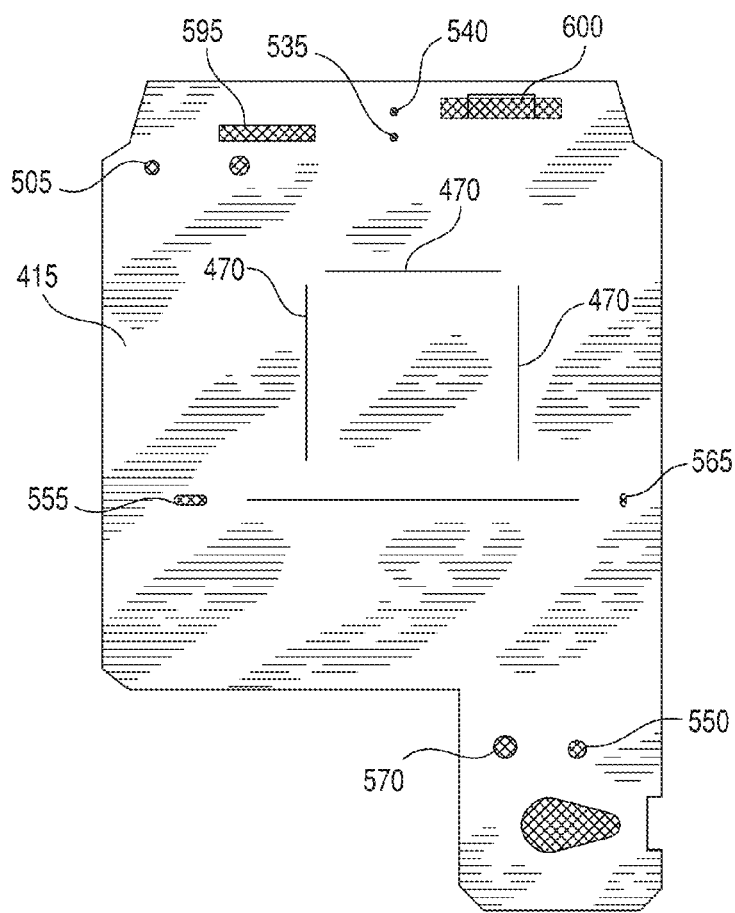
FIG. 10 shows a top view of a tape gasket in accordance with some aspects of the invention.
Figure 11:
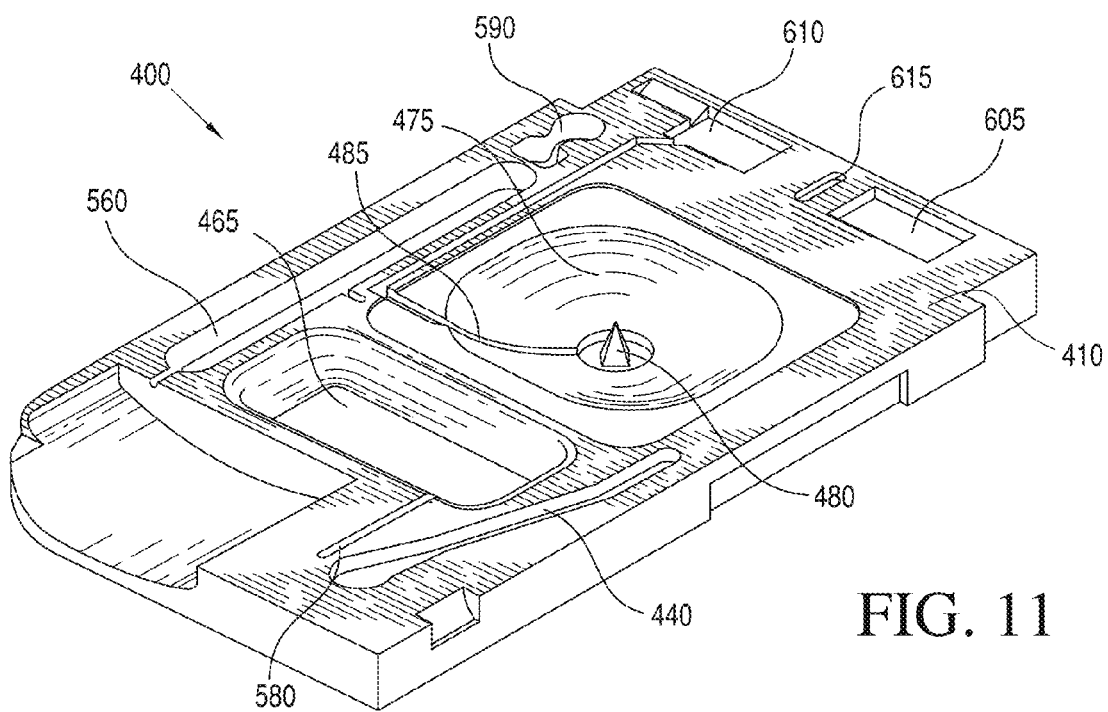
FIG. 11 shows an isometric top view of a biosensor cartridge base in accordance with some aspects of the invention.

In one embodiment, as shown in FIGS. 8-11, a cartridge 400 (e.g., a disposable assay cartridge) may comprise a cover 405 (as shown in FIGS. 8 and 9), a base 410 (as shown in FIG. 11), and a thin-film adhesive gasket 415 (as shown in FIG. 10) that is disposed between the base 410 and the cover 405. The cartridge 400 may be configured for insertion into a reader device, and therefore the cartridge 400 may comprise a plurality of mechanical and electrical connections (not shown) for this purpose. Advantageously, a feature of the cartridge 400 is that once a sample is loaded within the cartridge 400, analysis of the sample may be completed and the cartridge 400 may discarded without an operator or others contacting the sample.

Referring to FIG. 8, the cover 405 may be made of a rigid material, preferably plastic, and capable of repetitive deformation at flexible hinge regions 420, 425, and 430 without cracking. The cover 405 may comprise a lid 435, attached to a main body of the cover 405 by the flexible hinge 425. In operation, after introduction of a sample into a sample holding chamber 440 (as shown in FIG. 11) through a sample entry port 445, the lid 435 may be secured over an entrance to the sample entry port 445, preventing sample leakage. The lid 435 may be held in place by a hook 450.

The cartridge 400 optionally may also have a closure feature as described in jointly owned U.S. Pat. No. 7,682,833, which is hereby incorporated by reference in its entirety, for sealing the sample entry port 445 in an air-tight manner. This closure device may be slidable with respect to a body of the cartridge 400 and provides a shearing action that displaces excess sample located in the region of the sample entry port 445, reliably sealing a portion of the sample in the sample holding chamber 440 between the sample entry port 445 and a capillary stop. Specifically, the cartridge 400 may be sealed by slidably moving a sealing element over the surface of the cartridge in a manner that displaces excess fluid sample away from the sample entry port 445, seals a volume of the fluid sample within the internal fluid sample holding chamber 440, and inhibits fluid sample from prematurely breaking through the internal capillary stop.

The cover 405 may further comprise two paddles 455 and 460 that are moveable relative to the body of the cover 405, and which are attached to the cover 405 by the flexible hinge regions 420 and 430. The paddle 460 may be configured to be operated by a pumping means such that a force is exerted upon an air bladder comprised of cavity 465 (as shown in FIG. 10) and the gasket 415. Operation of the paddle 460 displaces fluid within conduits of the cartridge 400.

The paddle 455 may be configured to be operated upon by a second pumping means such that a force is exerted upon the gasket 415, which can deform because of slits 470 cut therein (as shown in FIG. 10). Deformation of the gasket 415 may transmit pressure onto a fluid-containing foil pack filled with a fluid, e.g., approximately 130 μL of analysis/wash solution or fluid, located in cavity 475 (as shown in FIG. 11), rupturing the foil pack upon spike 480, and expelling fluid into conduit 485. The conduit 485 may be connected via a short transecting conduit in the base 410 to a conduit 490 (as shown in FIG. 9). The fluid fills a front of the conduit 485 first pushing fluid into a small opening in the gasket 415 that acts as a capillary stop.

Additional action in the cartridge 400 generated by mechanisms within the reading device applied to the cartridge 400 may be used to inject one or more air segments into the fluid at controlled positions within the conduit 490. The air segments may be used to wash a sensor surface of the sensor array and the surrounding conduit 490 with a minimum amount of fluid. For example, the cover 405 may further comprise a hole covered by a thin pliable film 495. In operation, pressure exerted upon the film 495 may expel one or more air segments into the conduit 490 through a small hole 505 in the gasket 415 (as shown in FIGS. 9 and 10).

Referring to FIG. 9, a lower surface of the cover 405 further comprises the conduit 490 and another conduit 510. The conduit 490 includes a constriction 520 that controls fluid flow by providing resistance to the flow of the fluid. Optional coatings 525 and 530, e.g., dry reagent coatings, may provide hydrophobic surfaces on the conduit 510, which together with gasket holes 535 and 540 control fluid flow between conduits 190 and 510. A recess 545 in the base may provide a pathway for air to enter and/or escape the conduit 440 through hole 550 in the gasket.

Referring to FIG. 10, the thin-film gasket 415 comprises various holes and slits to facilitate transfer of fluid and air between conduits within the base 405 and the cover 410, and to allow the gasket 415 to deform under pressure where necessary. Specifically, a hole 555 may permit fluid to flow from the conduit 490 into a waste chamber 560, a hole 565 may comprise a capillary stop between conduits 440 and 510, a hole 570 may permit air to flow between a recess 575 (as shown in FIG. 9) and a conduit 580 (as shown in FIG. 10), the hole 550 provides for air movement between the recess 545 and the conduit 440, and the hole 505 permits fluid to flow from a conduit 585 (as shown in FIG. 9) to the waste chamber 560 via optional closeable valve 590 (as shown in FIG. 11). Holes 595 and 600 permit a plurality of electrodes that are housed within cutaways 605 and 610, respectively, to contact fluid within the conduit 490. In a specific embodiment, cutaway 610 houses a ground electrode, and/or a counter-reference electrode, and cutaway 605 houses at least one analyte sensor, and optionally, a reference sensor.

Referring to FIG. 11, the conduit 440 may be configured as a sample holding chamber that connects the sample entry port 445 to the conduit 510 in the assembled cartridge 400. The cutaway 605 may house at least one analyte sensor (e.g., the pair of electrodes), or an analyte responsive surface, together with an optional conductimetric sensor or sensors. The cutaway 610 may house a ground electrode if needed as a return current path for an electrochemical sensor, and may also house an optional conductimetric sensor. A cutaway 615 may provide a fluid path between gasket holes 535 and 540 such that fluid may pass between the conduits 490 and 510. Recess 475 houses a fluid-containing package, e.g., a rupturable pouch, in the assembled cartridge 400 that may be pierced by the spike 480 because of pressure exerted upon paddle 455 upon insertion of the cartridge 400 into the reading device. Fluid from the pierced package flows into the conduit 485. The air bladder may be comprised of the recess 465, which is sealed on its upper surface by the gasket 415. The air bladder may be one embodiment of a pump means, and may be actuated by pressure applied to the paddle 460, which displaces air in the conduit 580 and thereby displaces the sample from the sample chamber 440 into the conduit 510.

In some embodiments, a metering means may optionally comprise the sample chamber 440 bounded by the capillary stop 565 and having along the chamber 440 length an air entry point (gasket hole 550) from the bladder. Air pressure exerted at the gasket hole 550 drives a metered volume of the sample past the capillary stop 565. Therefore, a metered volume of sample may be predetermined by a volume of the sample chamber 440 between the air entry point 550 and the capillary stop 565. An amount of the sample corresponding to this volume may be displaced into the conduit 510 when the paddle 460 is displaced. This arrangement may therefore provide a metering means for delivering a metered amount of an unmetered sample into the various downstream conduits of the cartridge 400. The metering may be advantageous in some embodiments if quantitation of the analyte is required. Thus, an operator may be relieved of accurately measuring the volume of the sample prior to measurement saving time, effort, and increasing the accuracy and reproducibility.

Figure 12:
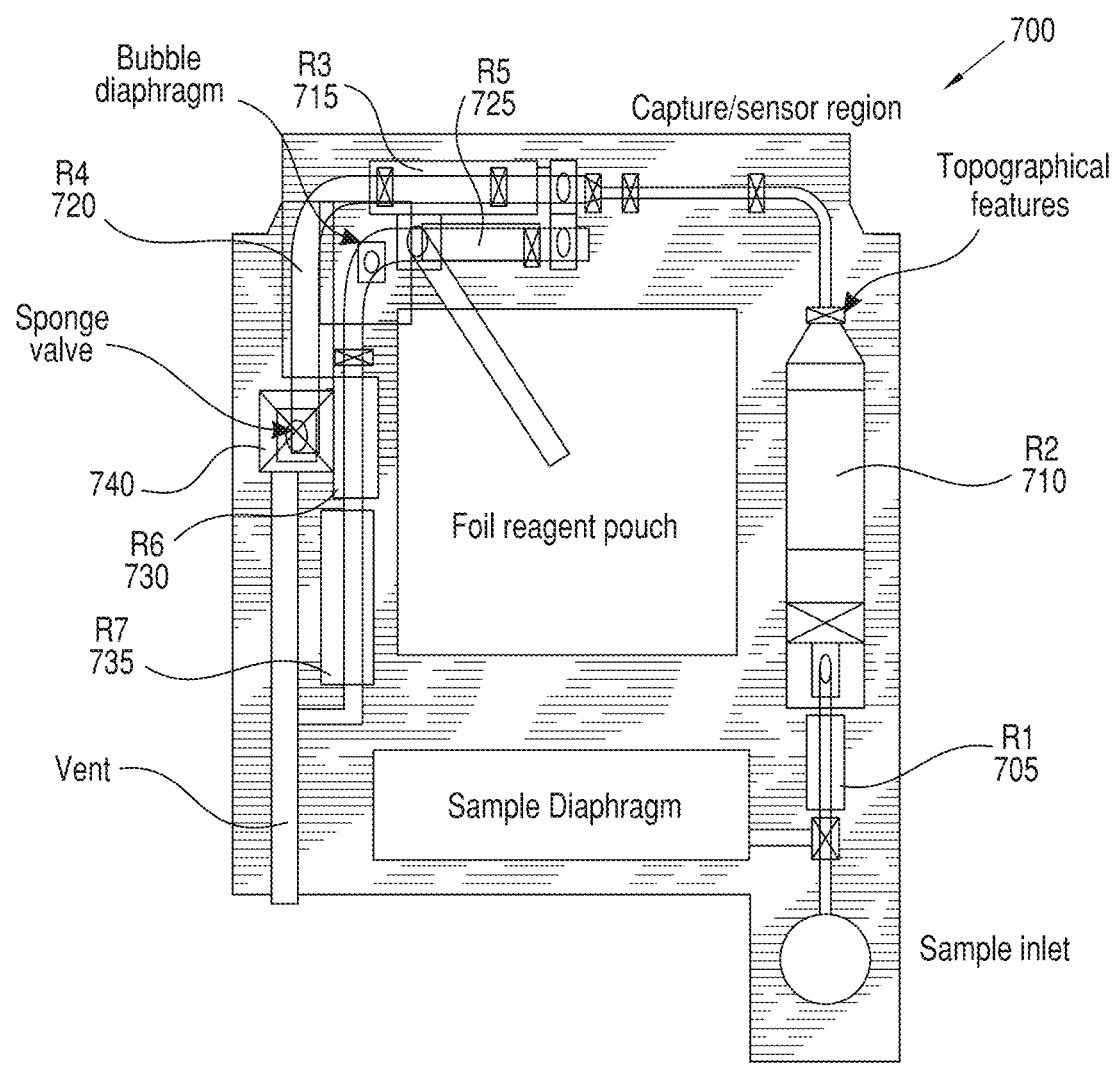
FIG. 12 shows a schematic view of the layout of a biosensor cartridge in accordance with some aspects of the invention.
Figure 15:
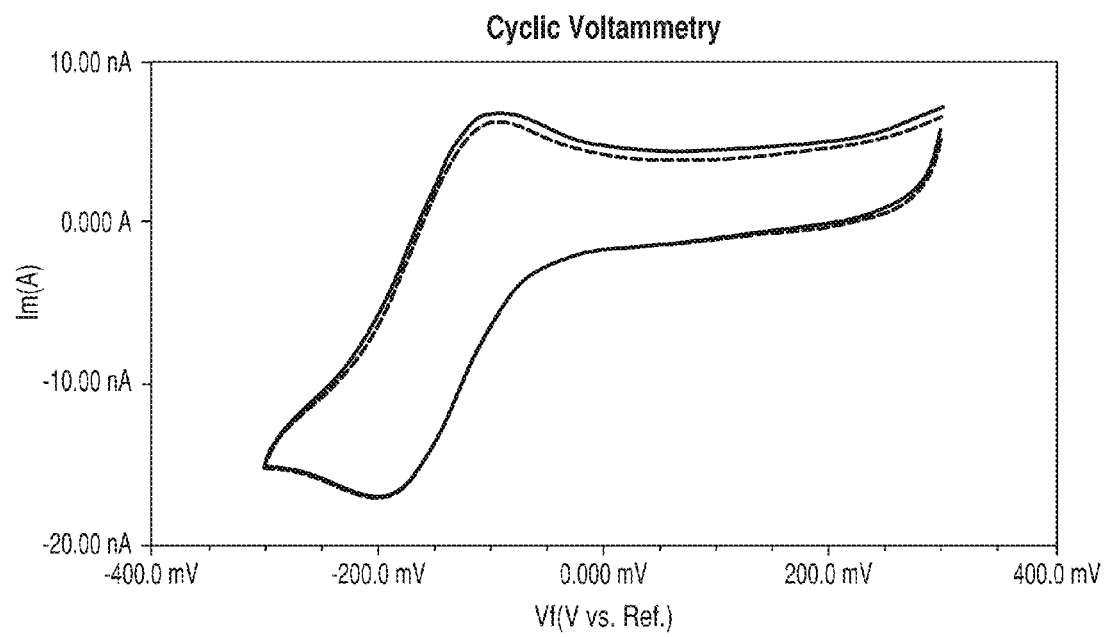
FIG. 15 shows cyclic voltammetry data of a commercial microbial sarcosine oxidase from Toyoba in accordance with some aspects of the invention.
Figure 16:
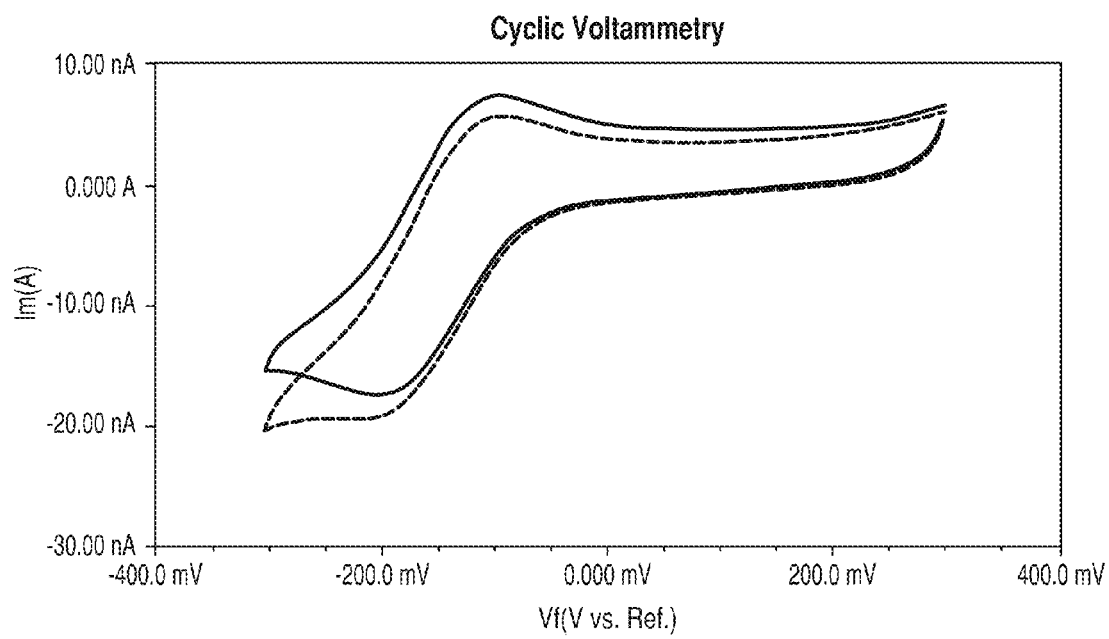
FIG. 16 shows cyclic voltammetry data of the recombinant wild type sarcosine oxidase in accordance with some aspects of the invention.
Figure 17:
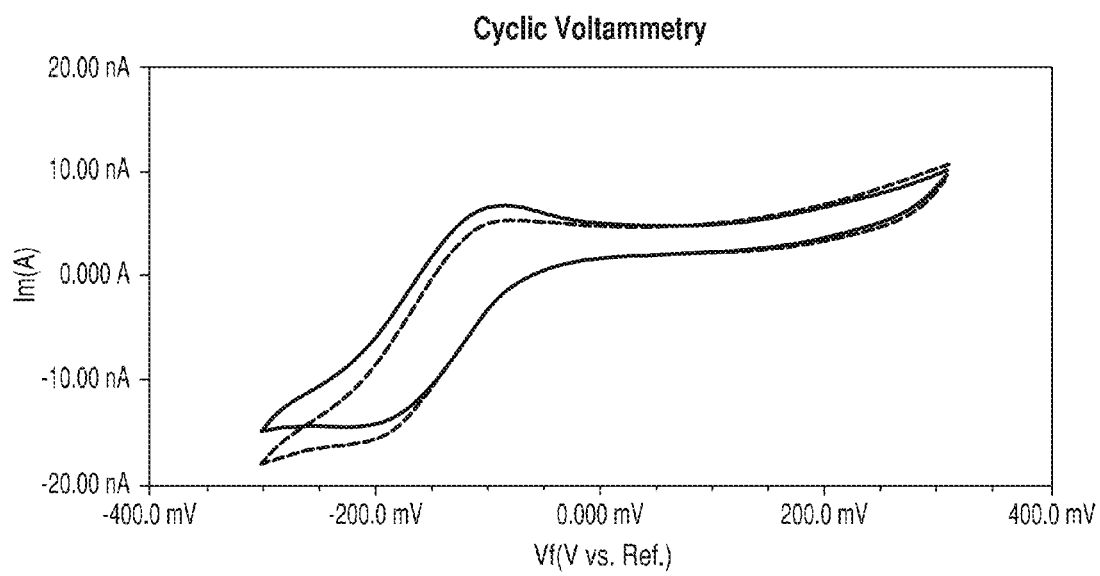
FIG. 17 shows cyclic voltammetry data of the FQ1-3 sarcosine oxidase mutation in accordance with some aspects of the invention.
Figure 18:
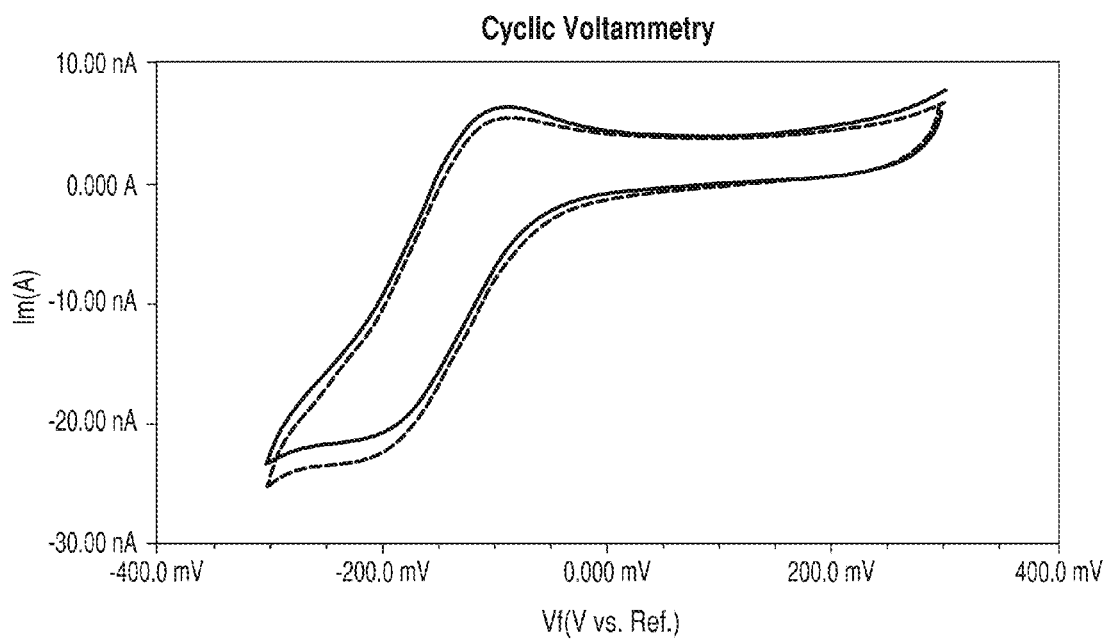
FIG. 18 shows cyclic voltammetry data of the FM1-3 sarcosine oxidase mutation in accordance with some aspects of the invention.
Figure 19:
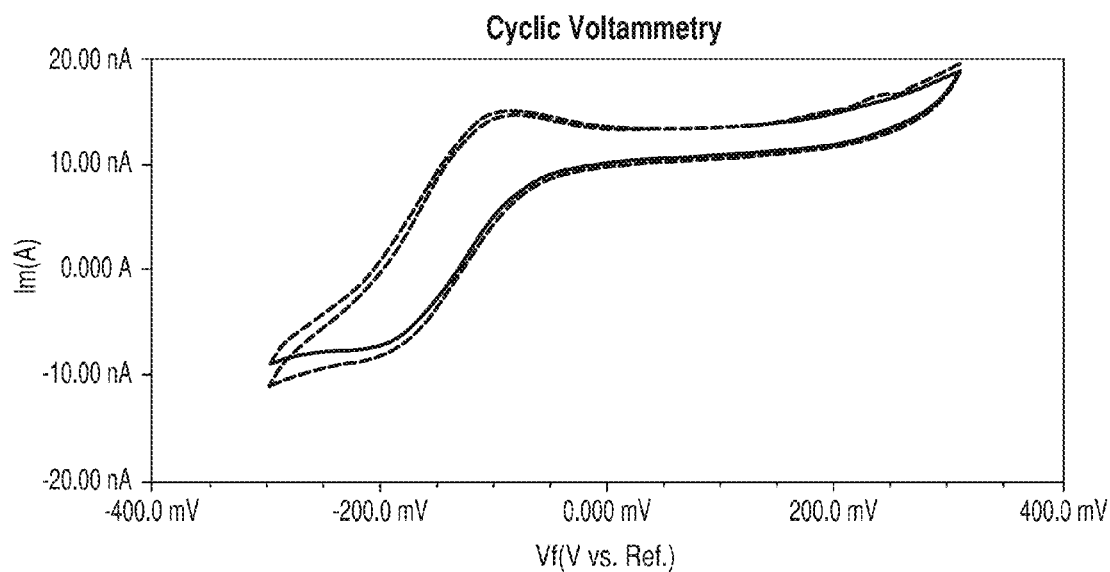
FIG. 19 shows cyclic voltammetry data of the FA1-4 sarcosine oxidase mutation in accordance with some aspects of the invention.
Figure 20:
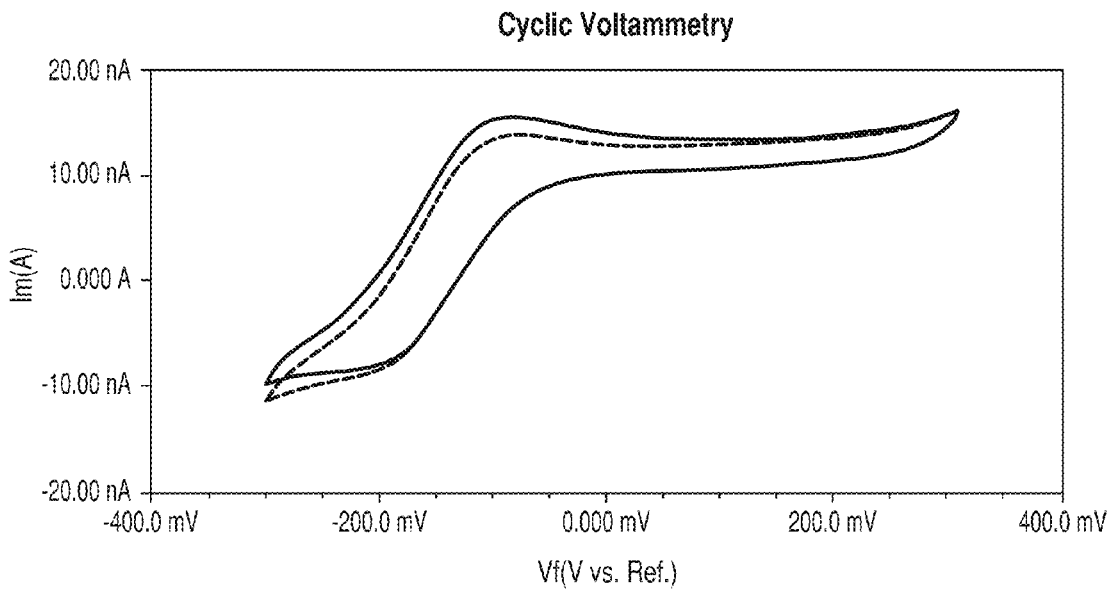
FIG. 20 shows cyclic voltammetry data of the FR1-4 sarcosine oxidase mutation in accordance with some aspects of the invention.

As shown in FIG. 12, a schematic diagram of the features of the cartridge 700 and components therein is provided. Specifically, in preferred embodiments, the conduits and the sample chamber 705-735 may be coated with dry reagents to amend the sample or fluid as discussed herein. The sample or fluid may be passed at least once over the dry reagent to dissolve the dry reagent. Reagents that may be used to amend samples or fluid within the cartridge include enzymes, a water soluble protein, a buffer, scavengers, or combinations thereof, and/or blocking agents that prevent either specific or non-specific binding reactions among assay compounds. A surface coating that may not be soluble but helps prevent non-specific adsorption of assay components to the inner surfaces of the cartridge 700 may also be provided For example, within a segment of the sample or fluid, an amending substance may be preferentially dissolved and concentrated within a predetermined region of the segment. In one embodiment, this may be achieved through control of the position and movement of the segment within the conduits and the sample chamber 705-735. Therefore, if only a portion of a segment, such as the leading edge, is reciprocated over the amended substance, then a high local concentration of the substance can be achieved close to the leading edge. Alternatively, if a homogenous distribution of the substance is desired, for example if a known concentration of an amending substance is required for a quantitative analysis, then further reciprocation of the sample or fluid may result in mixing and an even distribution.

In preferred embodiments, a closeable valve 740 may be provided between a first conduit and the waste chamber. In one embodiment, the valve 740 may be comprised of a dried sponge material that is coated with an impermeable substance. In operation, contacting the sponge material with the sample or a fluid may result in swelling of the sponge to fill the cavity (e.g., the valve 590 cavity as shown in FIG. 11), thereby substantially blocking further flow of liquid into the waste chamber. Furthermore, the wetted valve 740 may also be configured to block the flow of air between the first conduit and the waste chamber, which permits a first pump means connected to the sample chamber to displace fluid within a second conduit, and to displace fluid from the second conduit into the first conduit in the following manner.

After the sample is exposed to the sensor array for a controlled time, the sample may be moved into a post-analytical conduit where the sample may be amended with another reagent. The sample may then be moved back to the sensor array and a second reaction period may begin. Alternately, the post-analysis conduit may serve simply to separate the sample segment from the sensor array. Within the post-analysis conduit may be a single closeable valve that connects an air vent of the sensor conduit to a diaphragm air pump. When the single closeable valve closes, the sample may be locked in the post analytical conduit and cannot be moved back to the sensor array.

In a preferred embodiment of the present invention, the sample and a fluid, e.g., a combined wash and substrate delivery fluid, may contact the sensor array at different times during an assay sequence. The sample and the fluid may also be independently amended with other reagents or compounds present initially as dry coatings within respective conduits of a test device, e.g., the cartridge. Controlled motion of the fluid by the above-described pumping means within the cartridge further permits more than one substance to be amended into each fluid whenever the sample or the fluid is moved to a new region of the conduit. In this manner, multiple amendments to each fluid may be accommodated, extending the complexity of automated assays that can be performed in the cartridge. Therefore, the utility of the present invention may be enhanced.

In an alternative embodiment, as shown in FIGS. 13A-13E, the cartridge 900 may include a housing that comprises two complimentary halves of a cartridge (e.g., the cover 901 and the base 902), which can be bonded together to abut and attach the two complimentary interior surfaces of the two halves in a closed position. In some embodiments, the cover 901 and the base 902 are injection molded, for example, by machine as disclosed in U.S. patent application Ser. No. 13/530,501, filed on Jun. 22, 2012, which is incorporated herein by reference in its entirety. Preferably, the cover 901 is injection molded where a first substantially rigid zone 920 is formed in a first injection molding step and a substantially flexible zone 922 is formed in an additional injection molding step. Preferably, the base 902 is injection molded where a second substantially rigid zone 924 is formed in a first injection molding step.

As shown in FIGS. 13A-13E, the substantially rigid zones 920 and 924 of the cover 901 and the base 902, respectively, are preferably each a single contiguous zone; however, the molding process can provide a plurality of non-contiguous substantially rigid zones. The substantially flexible zone 922 is preferably a set of several non-contiguous zones. For example, the substantially flexible zone 922 around a displaceable membrane 925 may be separate and distinct from the substantially flexible zone at a closeable sealing member 928. Alternatively, the substantially flexible zone may comprise a single contiguous zone.

In a preferred embodiment, the cartridge housing comprises a sensor recess 930 in a portion of the substantially flexible zone. An advantage is that the sensors 935, which are disposed in the sensor recess 930 preferably are made on a silicon wafer substrate, which is relatively brittle. Thus, providing a substantially flexible sensor recess 930 results in a suitable support that can protect the sensor from cracking during assembly. Note that other non-silicon based sensors may be used, e.g., those made on a plastic substrate; however, the preferred embodiment uses sensors of the type described in U.S. Pat. Nos. 5,200,051; 5,514,253; and 6,030,827, the entireties of which are incorporated herein by reference. In addition to being substantially flexible, sensor recess 930 may be best selected to form a liquid-tight and/or air-tight seal around the sensor perimeter, thereby ensuring that liquids do not leak out of the conduit that covers the sensor in the fully assembled cartridge. In an alternative embodiment, sensor recess 930 can be formed in a portion of the substantially rigid zone (as shown in FIG. 11) of either or both of the cover or the bottom of the housing. In this aspect, a liquid-tight and/or air-tight seal optionally may be formed by the double-sided adhesive sheet 415 or gasket (as shown in FIG. 10).

With regard to overall dimensions, the preferred embodiment of the molded parts shown in FIGS. 13A-13E include the cover 901 with dimensions of about 6.0 cm×3.0 cm×0.2 cm and the base 902 with dimensions of about 5.0 cm×3.0 cm×0.2 cm to provide a cartridge 900 with dimensions of about 6.0 cm×3.0 cm×0.4 cm. In terms of ranges, the cartridge 900 optionally has a length of from 1 to 50 cm, e.g., from 5 to 15 cm, a width of from 0.5 to 15 cm, e.g., from 1 to 6 cm, and a thickness of from 0.1 to 2 cm, e.g., from 0.1 to 1 cm.

Processes for Target Analyte Detection Using a Hybrid Enzyme

In preferred embodiments, the invention is a process for using a cartridge to determine the presence and/or concentration of a target analyte in a sample. The process may include introducing an unmetered fluid sample into the sample chamber 440 of the cartridge 400 through the sample entry port 445 (as shown in FIGS. 8-11). Capillary stop 565 prevents passage of the sample into conduit 510 at this stage, and conduit 440 is filled with the sample. Lid 435 is closed to prevent leakage of the sample from the cartridge. The cartridge may then be inserted into the reading device or apparatus 302, as shown in FIG. 7 and further disclosed in U.S. Pat. No. 5,821,399, which is incorporated herein by reference in its entirety. Insertion of the cartridge into the reading apparatus activates a mechanism, which punctures the fluid-containing package located at recess 475 when the package is pressed against spike 480. Fluid is thereby expelled into the conduits 485 and 490, arriving in sequence at the sensor region. The constriction 520 prevents further movement of fluid because residual hydrostatic pressure is dissipated by the flow of fluid via the conduit 585 into the waste chamber 560.

In a second step, operation of a pump means applies pressure to the air-bladder comprised of cavity 465, forcing air through the conduit 580 and into conduit 440 at a predetermined location. Capillary stop 565 delimits a metered portion of the original sample. While the sample is within sample chamber 440, it is preferably amended with a compound or compounds (e.g., enzymes, a water soluble protein, a buffer, scavengers, or a combination thereof) present initially as a dry coating or layer(s) on the inner surface of the chamber or conduits. The metered portion of the sample is then expelled through the capillary stop 565 by air pressure produced within air bladder comprised of cavity 465. The sample passes into the sensor conduit and into contact with the biosensor located within the cutaway 605.

To promote reaction of the target analyte or cognate molecule in the sample with the hybrid enzyme immobilized on or near the electrodes, the sample containing the analyte (e.g., creatinine) may optionally be passed repeatedly over the electrodes in an oscillatory motion. Preferably, an oscillation frequency of between about 0.2 and 2 Hz is used, most preferably 0.7 Hz. After a period, e.g., 10 minutes, for catalysis of the reaction using the hybrid enzyme, the sample may be ejected by further pressure applied to the air bladder comprised of cavity 465, and the sample passes to waste chamber 560. A wash step next removes any remaining analyte or cognate molecule from the sensor chamber. Fluid in the conduit 490 may be moved by a pump means, into contact with the sensors. The analysis fluid (e.g., cognate molecule) may be pulled slowly until a first air segment is detected at a conductivity sensor. Note that it may be an object of the invention that the rinsing is not sufficiently protracted or vigorous as to promote dissociation of the hybrid enzyme from the sensors.

Use of a cartridge with a closeable valve, preferably located between the sensor chamber and the waste chamber, is herein illustrated by a specific embodiment in which the concentration of creatinine is determined within a blood sample, which is introduced into the sample chamber of said cartridge. In the following time sequence, time zero (t=0) represents the time at which the cartridge is inserted into the cartridge reading device. Times are given in minutes. Between t=0 and t=1.5, the cartridge reading device makes electrical contact with the electrodes/sensors through pads, and performs certain diagnostic tests. Insertion of the cartridge perforates the foil pouch introducing fluid into a conduit as previously described. The diagnostic tests determine whether fluid or sample is present in the conduits using the conductivity electrodes; determine whether electrical short circuits are present in the electrodes; and ensure that the biosensor and ground electrodes are thermally equilibrated to, preferably, 37° C. prior to the analyte determination.

Various options exist for managing any temperature effect on an assay of this type. For example, the assay can be run in a system where the sample and other fluids and reagents are thermostated at a given temperature, e.g., 37° C. Alternatively, the assay may be run at ambient temperature, without any correction, or with correction to a standardized temperature based on measurement of the ambient value Between t=1.5 and t=6.75, a metered portion of the sample, preferably between 4 and 200 uL, more preferably between 4 and 20 uL, and most preferably 7 uL, may be used to contact the electrodes/sensors as described above. The edges defining the forward and trailing edges of the sample are reciprocally moved over the sensor region at a frequency that is preferably between 0.2 to 2.0 Hz, and is most preferably 0.7 Hz. During this time, any target analyte or cognate molecule in the sample may be acted upon by the hybrid enzyme, as previously described.

Between t=6.75 and t=10.0 the sample may be moved into the waste chamber via the closeable valve, preferably wetting the closeable valve and causing it to swell and close. The seal created by the closing of the valve permits the first pump means to be used to control motion of fluid from the sensor conduit to the post analysis conduit. After the valve closes and any remaining sample is locked in the post analysis conduit, the analyzer plunger retracts from the flexible diaphragm of the pump means creating a partial vacuum in the sensor conduit. This forces an analysis fluid (e.g., a substrate) through the small hole in the tape gasket and into a short transecting conduit in the base. The analysis fluid is then pulled further and the front edge of the analysis fluid is oscillated across the surface of the sensor chip in order to shear the sample near the walls of the conduit. A conductivity sensor on the sensor chip may be used to control this process. The efficiency of the process may be monitored using the amperometric sensors. The amperometric electrodes may be polarized to 0.06 V versus the silver chloride reference-ground electrode. In this embodiment, the fluid may be composed of a carbonate or diethanolamine buffer and a substrate. The efficiency of the wash is optimally further enhanced by introduction into the fluid of one or more segments that segment the fluid within the conduit as previously described. Following removal of wash fluid from the sensor channel leaving a thin layer of fluid over the two sensors, measurement of each sensor response is recorded and the concentration of analyte determined as described above.

EXAMPLES

For purposes of illustration and not limitation, the following examples provide information on a sarcosine oxidase and bilirubin oxidase enzyme based sensor, which has enhanced ability to transfer electrons to a suitable mediator instead of a natural electron acceptor.

Example 1

Design and Expression of Recombinant Wild-Type Sarcosine Oxidase

Using a wild-type protein sequence from *Bacillus* spp. B-0618 sarcosine oxidase (UniProt database accession P40859), the protein sequence was reverse translated back to DNA SEQ ID NO:1 using high expression codons found for *Escherichia coli* (www.kazusa.or.jp). An EcoRI adaptor site was added to the 5'-end, and a HindIII adaptor site was added to the 3'-end of the gene. The adaptor sequences generate an in-frame fusion in a pET28b+ vector, fusing the hexahistidine tag (SEQ ID NO: 34) found in the vector. The pET28b+ vector was cleaved with EcoRI/HindIII and dephosphorylated. The gene sequence with adaptors was synthesized by GenScript (860 Centennial Ave., Piscataway, N.J., 08854, USA) and cloned into the pET28b+ vector using T4 DNA Ligase, followed by transformation into an *E. coli* host organism. The construct is provided as a DNA construct which is transformed into BL21(DE3) *E. coli* host on 2×YT plates containing 50 ug/mL Kanamycin.

One transformant was selected and grown in 2×YT broth containing 50 ug/mL Kanamycin until an OD600 absorbance of 0.5. Indophenol galactopyranoside (IPTG) Inducer is added to a final concentration of 1 mM and let continue to grow at 30° C. for a minimum of 3 hours. The cells were pelleted by centrifugation at 5000 RPM for 10 minutes. The cells may then be frozen at this point at −20° C. for overnight and be resuspended in CelLytic™ B Cell Lysis Reagent with 0.5 mg/ml of lysozyme the next day. The cell lysate can then be centrifuged at 5000 RPM for 10 minutes and the supernatant can be used directly for enzyme assays, or can be further purified by running through a nickel column and eluting the protein as a nearly homogenous preparation by using a high concentration imidazole (300 mM to 500 mM) step gradient. The elution fraction needs to be run through a desalting column and buffer exchanged to PBS buffer and concentrated. This preparation can then be stored at 4° C. until ready to use.

Example 2

Sarcosine Oxidase (SOX) Mutagenesis

Using the Recombinant Sarcosine Oxidase clone from Example 1 as the starting material, four site specific mutations were generated. The mutations were generated using synthetic mutagenic primers SEQ ID NOS: 2 to 6 with a slight modification of the Thermo Scientific Phusion Site-Directed Mutagenesis Kit (F-541). Essentially SEQ ID NOS: 2 to 5 comprising mutagenic primers were paired with the reverse primer SEQ ID NO: 6. The high fidelity Phusion Hot Start II DNA Polymerase was used to generate a mutagenized amplicon having 5'-phosphorylated ends. The kit was modified by using NEB T4 DNA ligase and performing the ligation reaction overnight at 16° C., instead of the kits rapid ligation reagents and protocol. The ligated material was then transformed into the BL21(DE3) cells. The mutants were confirmed by sequencing or restriction fragment length polymorphism (PstI with the Glutamine mutation). The cells were then grown in flasks with 2×YT broth containing 50 ug/mL Kanamycin and induced as described in Example 1. The designations of the mutations are shown in FIG. 14. The sequence of the arginine mutant is shown in SEQ ID NO: 7.

Example 3

Engineered SOX-Mediator Experiment

A commercially available 65 KDa SOX (Toyobo), a recombinant clone of wild type 48 KDa SOX (from Example 1) as well as 4 other single point mutation clones of the 48 KDa SOX (from Example 2) were tested for their ability to transfer electrons to an Osmium redox mediator. The 4 clones (see FIG. 14) of SOX were designated as SOXFM1-3, SOXFQ1-3, SOXFR1-x and SOXFA1-4. These mutations were designed to prevent the clone from interacting with the Flavin Adenine Dinucleotide (FAD) responsible for the transfer of electrons to oxygen. The SOX clone would however be able to extract electrons from the Sarcosine substrate as the FAD cofactor that receives the electrons (substrate FAD) is still present in the clones. Because the clones are unable to efficiently transfer electrons to oxygen, the FAD cofactor is expected to stay in a reduced state for a prolonged period thereby allowing time for the mediator to pick up electrons from the reduced form of the enzyme. In addition, they have the potential to alter the ability of the redox mediator to approach the substrate FAD due to steric hinderance considerations, as the point mutations may slightly alter the 3D structure of the enzyme.

Cyclic voltammetry (CV), using a gold working electrode was used to assess if the mediator is being reduced by the enzyme. The observed result, when the substrate is present, is that as the mediator is reduced by the enzyme the oxidation peak current is increased. Given that the sarcosine substrate is added in excess, the rate at which the mediator is reduced is dependent upon the concentration of the enzyme activity and the efficiency of electron transfer to the mediator. FIG. 5 shows a schematic of the biosensor set up used in this example. For this example Osmium bis(bipyridine)-4-(methylamino)pyridine (OsBPP) was used as the redox mediator.

To observe if electron transfer is taking place a 600 µL solution containing 0.5 mg/mL OsBPP and 2 mg/mL sarcosine made up in HEPES buffered saline was pipetted into the electrochemical cell, the working electrode was a 0.5 mm diameter gold working electrode, the counter electrode was a gold wire and the reference was a Ag/AgCl with a saturated KCl junction. This was followed by the addition of 60 µl of one of the test enzyme preps, which was thoroughly homogenized by pipette. The SOX activity of the 65 KDa solution was 127 U/mL and the 48 KDa solution was 263 U/mL, using a horseradish peroxidase/tetramethylbenzidine coupled assay. Units are µmol of $H_2O_2$/minute. The mutants were observed to generate 0 U/ml of activity in this coupled assay, because the mutants are not able to transfer electrons to Oxygen. Their comparative activity was not determined directly, but based upon protein analysis the concentration of the mutants in each unpurified preparation were less than the concentration of the wild type enzymes. It is assumed for this comparison that the enzymatic activity of the mutants is the same as the wild type.

Figures 21, 22:
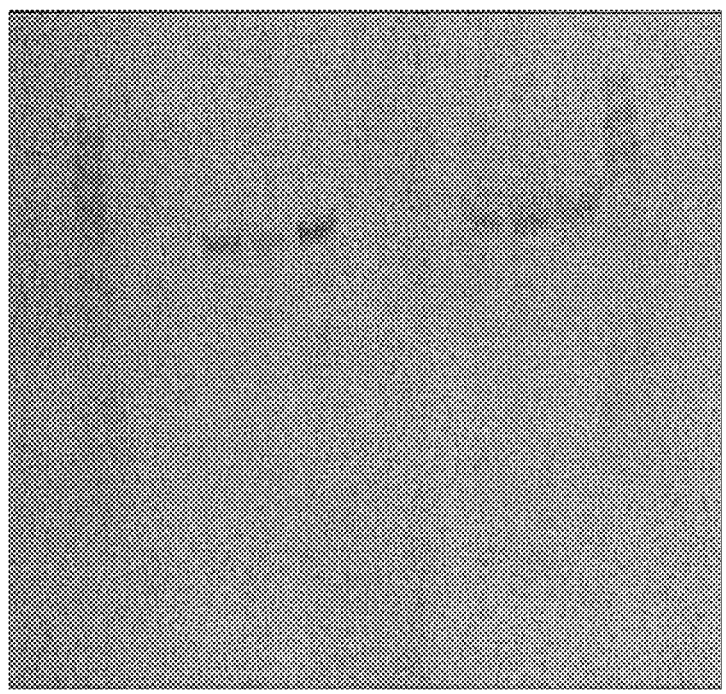
FIG. 21 shows the redox potentials of the analyzed sarcosine mutants in accordance with some aspects of the invention.
FIG. 22 shows Western analysis of a recombinant bacterial bilirubin oxidase using a hexahistidine ("hexahistidine" disclosed as SEQ ID NO: 34) antibody in accordance with some aspects of the invention.

Two sets of CVs were performed, from 0.3 to −0.3V, each set consisting of 3 cycles. The voltage scan rate in the CVs was maintained at a slow scan rate of ~10 mV/s, which showed a pronounced effect and cut the background current. The first set was done immediately after the addition of the enzyme. The second set was done after the solution was incubated for 5 minutes. FIGS. 15 through 20 show the second scan CV of each set for each of the enzyme preparations tested. To quantify the relative degree of electron transfer the ratio of the oxidation peak currents of the second scan for the initial set of CVs and 5 minute incubation CV set were calculated (see FIG. 21). The higher the ratio the greater the amount of electron transfer from the enzyme to the mediator. It was found that electron transfer to the 48 kD wild type SOX was significantly greater than for the 65 kD wild type. The FM1-3, FA1-4 mutants exhibited decreased electron transfer, FQ1-3 exhibited similar electron transfer to the wild type and FR1-4 exhibited enhanced electron transfer. Factoring in the enzyme activity the electron transfer rate of the 48 kD wild type enzyme is approximately 2 times that of the 65 kD wild type SOX and the FR1-4 clone is at least 5 times.

Example 4

Conjugated SOX Bead Preparation and Dispensing

The SOX beads were prepared as follows: 15 mg of 1.01 μm carboxylated polystyrene microparticles (10% weight/volume) (part# PCO4N, Bangs Laboratories Inc., USA), were reacted with 2 mg of SOX protein in 25 mM 2-(N-morpholino) ethanesuifonic acid (MES buffer, pH 6.2) for 15 minutes, and then were centrifuged to remove the supernatant. After resuspension of the pellet in 25 mM MES buffer, 10 mM carbodiimide (EDAC) was added to the sample and reacted for 2 hours at 4° C. This was followed by centrifuging the sample, washing the pellet with ⅕ physiological phosphate buffer twice. A formulated sample with 10% solids in phosphate buffer including 0.05% Tween 20 was stored for further use.

These beads were used in the assembly of creatine detecting cartridges. The beads were formulated to 3.2% solids in ⅕ physiological phosphate buffer, including 25% protein stabilization solution (Cat#Q2030529P1, Gwent Group, Pontypool, United Kingdom). A formulation of 0.8% solid, 0.8% protein stabilization solution in 0.08% Tween-20 was printed on chips and built into creatine cartridges.

Example 5

BOX

Transformed pWD170-pET28b(+) synthesized by Genscript into BL21(DE3) competent cells and plated onto 2YT/Kan plates for single colonies. Inoculated 5 ml of BL21(DE)3/pWD170-3 overnight culture into 500 ml 2YT/KAN+0.25 mM CuSO4 and grew it at 37 C. Monitored the OD 600 until it reached OD 0.5. Then added 5 ml of 100 mM IPTG to the reaction and changed temperature to 24° C. and let the induction reaction happen for overnight (>12 hours). The next day, the sample was centrifuged and the cell pellet was kept at −20° C. for next step.

The cells were thawed in Qiagen NPI-10 buffer (50 mM NaH2PO4, 300 mM NaCl and 10 mM imidazole) plus 1 mg/mL lysozyme to disrupt the cell pellet and release the protein.

The soluble protein was electrophoresed on an SDS-PAGE gel and Western transferred onto a membrane. The membrane was hybridized first with an anti-hexahistidine antibody ("hexahistidine" disclosed as SEQ ID NO: 34), followed by using an ALP conjugate and staining with NBT/BCIP dye. The resulting Western Blot (see FIG. 22) demonstrates that a protein product was produced in this bacterial clone.

Figure 23:
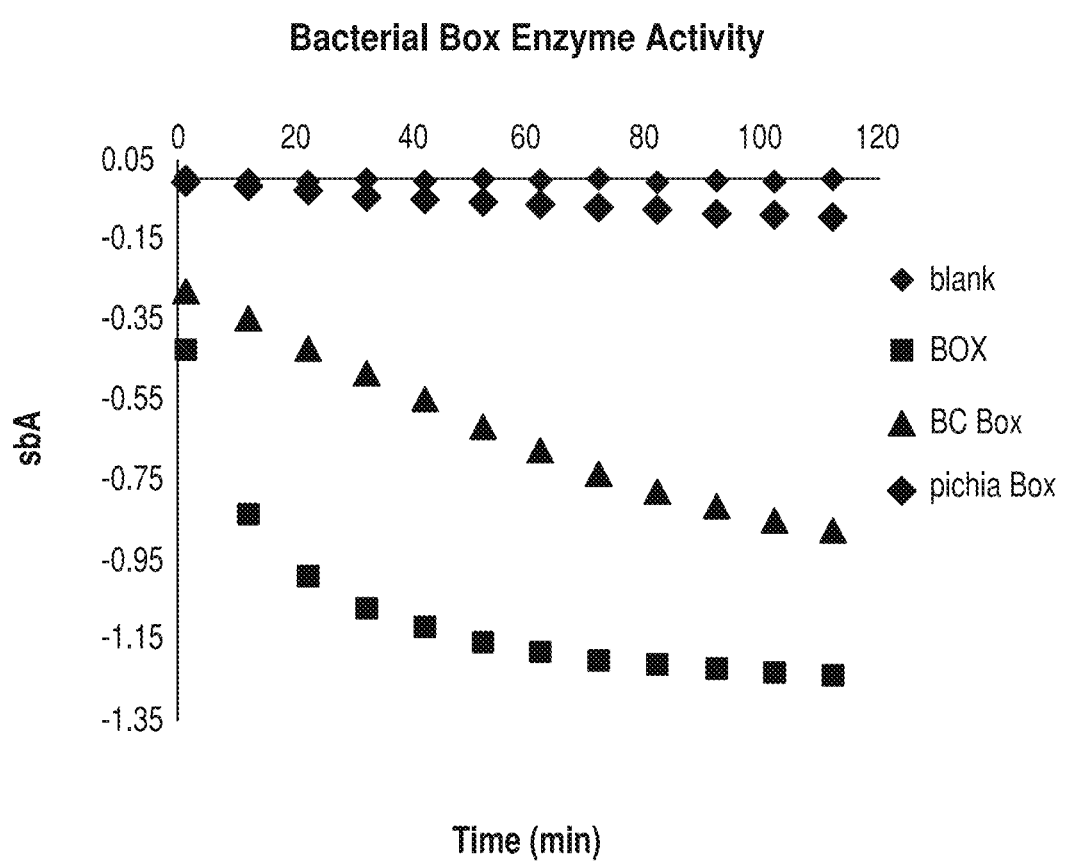
FIG. 23 shows bilirubin oxidase assays of native *Myrothecium verrucaria* Bilirubin Oxidase (BOX), *Pichia* recombinant BOX and bacterial cotA BOX preparations in accordance with some aspects of the invention.

The soluble protein was also tested in a bilirubin oxidase assay. A commercial preparation of native *Myrothecium verrucaria* enzyme, along with the *Pichia* bilirubin oxidase recombinant bilirubin oxidase were also tested in this assay. As shown in FIG. 23, higher enzyme activity of bilirubin oxidase assays of native *Myrothecium verrucaria* BOX, *Pichia* recombinant BOX, and bacterial cotA BOX preparations resulted in a lower absorbance over time. *Myrothecium verrucaria* mutations may be generated using synthetic mutagenic primers (SEQ ID NO: 10-22), and *Bacillus pumilus* cotA mutations may be generated using synthetic mutagenic primers (SEQ ID NO: 23-40).

While the invention has been described in terms of various preferred embodiments, those skilled in the art will recognize that various modifications, substitutions, omissions and changes can be made without departing from the spirit of the present invention. It is intended that the scope of the present invention be limited solely by the scope of the following claims. In addition, it should be appreciated by those skilled in the art that a plurality of the various embodiments of the invention, as described above, may be coupled with one another and incorporated into a single reader device.

We claim:

1. A device for detecting a target analyte, the device comprising:
   an electrochemical cell;
   an electron redox mediating molecule; and
   a recombinant modified enzyme engineered to:
      prevent transfer of electrons to a natural electron acceptor;
      transfer electrons to the electron redox mediating molecule; and
      provide enzymatic activity against the target analyte to generate an electrochemical signal dependent on a concentration of the target analyte in a sample.

2. The device of claim 1, wherein the natural electron acceptor is oxygen, nicotinamide adenine dinucleotide (NAD), or nicotinamide adenine dinucleotide phosphate (NADP).

3. The device of claim 2, wherein the sample comprises oxygen, NAD, or NADP.

4. The device of claim 1, wherein the detecting the target analyte does not require removal of oxygen from the sample.

5. The device of claim 1, wherein the target analyte is selected from the group consisting of sarcosine, glucose, lactose, creatinine, creatine, pyruvate, and bilirubin.

6. The device of claim 1, wherein the electron redox mediating molecule is selected from the group consisting of: ferrocene, ferrocene derivatives, ferrocyanide, quinone derivatives, osmium complexes, ruthenium complexes, transition metal complexes, iron organo complexes, polypyrrole and other conductive polymers, tetracyanoquinodimethane (TCNQ), and methylene blue and other organic dyes.

7. The device of claim 1, wherein the recombinant modified enzyme comprises a mutation of a protein coding sequence for a starting enzyme.

8. The device of claim 7, wherein the starting enzyme is selected from the group consisting of: an oxidoreductase, a transferase, a hydrolase, and a lyase.

9. The device of claim 7, wherein the recombinant modified enzyme is an oxidase with an inability to transfer electrons to oxygen.

10. The device of claim 7, wherein the starting enzyme is sarcosine oxidase and the mutation is a Lys265 to Arg265 mutation of the starting enzyme.

11. The device of claim 7, wherein the starting enzyme is a wild-type sarcosine oxidase produced by genus *Bacillus*.

12. The device of claim 7, wherein the protein coding structure is for sp-p40859 from *Bacillus* spp. Strain B-0618.

13. The device of claim 7, wherein the starting enzyme is sarcosine oxidase and the mutation is at a target site of the starting enzyme selected from the group consisting of: Arg49, Thr48, Gly344, Tyr317, Lys348, Arg52, His269, Tyr254, Met245, and Arg52.

14. The device of claim 7, wherein the staring enzyme is bilirubin oxidase and the mutation modifies an active site of the bilirubin oxidase for oxygen reduction and electron transfer to the natural electron acceptor of bilirubin oxidase located in a trinuclear cluster of bilirubin oxidase.

15. The device of claim 14, wherein the natural electron acceptor is dioxygen.

16. The device of claim 7, wherein the starting enzyme is a wild-type bilirubin oxidase produced by genus *Bacillus*.

17. The device of claim 7, wherein the protein coding structure is for spore coat protein gi-194015788 (ZP_03054403) from *Bacillus pumilus*.

18. The device of claim 10, wherein the starting enzyme is wild-type bilirubin oxidase produced from *Myrrothecium verrucaria* and the mutation is at a target site of the starting enzyme selected from the group consisting of: Cys457, His456, His458, His136, His134, His96, His403, His94, His401, Asp105.

19. A device for detecting a target analyte, the device comprising:
an electron redox mediating molecule; and
a recombinant modified enzyme comprising a mutation of a protein coding sequence for a starting enzyme,
wherein the mutation is engineered to modify an active site of the starting enzyme for oxygen reduction and electron transfer to a natural electron acceptor of the starting enzyme permitting transfer of electrons to the electron redox mediating molecule, and the recombinant modified enzyme maintains enzymatic activity against the target analyte.

20. An electrochemical biosensor, comprising:
a silver/silver chloride electrode connected to one end of a circuit;
a conductive metal surface connected to another end of a circuit; and
an immobilized enzyme layer comprising:
an electron mediator molecule; and
a recombinant modified enzyme lacking an ability to transfer electrons to a natural electron acceptor and instead transfers electrons to the electron mediator molecule such that the biosensor performs in a presence of oxygen.

* * * * *

SEQUENCE LISTING

<160> NUMBER OF SEQ ID NOS: 34

<210> SEQ ID NO 1
<211> LENGTH: 1182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaattcgtcc acccacttcg acgttatcgt tgttggtgct ggttccatgg gtatggctgc      60
tggttaccag ctggctaaac agggtgttaa aaccctgctg gttgacgctt tcgacccgcc     120
gcacaccaac ggttcccacc acggtgacac ccgtatcatc cgtcacgctt acggtgaagg     180
tcgtgaatac gttccgctgg ctctgcgttc ccaggaactg tggtacgaac tggaaaaaga     240

```
aacccaccac aaaatcttca ccaaaaccgg tgttctggtt ttcggtccga aaggtgaatc    300
cgctttcgtt gctgaaacca tggaagctgc taaagaacac tccctgaccg ttgacctgct    360
ggaaggtgac gaaatcaaca aacgttggcc gggtatcacc gttccggaaa actacaacgc    420
tatcttcgaa ccgaactccg tgttctgtt ctccgaaaac tgcatccgtg cttaccgtga     480
actggctgaa gctcgtggtg ctaaagttct gacccacacc cgtgttgaag acttcgacat    540
ctccccggac tccgttaaaa tcgaaaccgc taacggttcc tacaccgctg acaaactgat    600
cgtttccatg ggtgcttgga actccaaact gctgtccaaa ctgaacctgg acatcccgct    660
gcagccgtac cgtcaggttg ttggtttctt cgaatccgac gaatccaaat actccaacga    720
catcgacttc ccaggtttca tggttgaagt tccgaacggt atctactacg gtttcccgtc    780
cttcggtggt tgcggtctga aactgggtta ccacaccttc ggtcagaaaa tcgacccgga    840
caccatcaac cgtgagttcg tgtttaccc ggaagacgaa tccaacctgc gtgctttcct    900
ggaagaatac atgccgggtg ctaacggtga actgaaacgt ggtgctgttt gcatgtacac    960
caaaaccctg gacgaacact tcatcatcga cctgcacccg gaacactcca acgttgttat   1020
cgctgctggt ttctccggtc acggtttcaa attctcctcc ggtgttggtg aagttctgtc   1080
ccagctggct ctgaccggta aaaccgaaca cgacatctcc atcttctcca tcaaccgtcc   1140
ggctctgaaa gaatccctgc agaaaaccac catctgaagc tt                      1182

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cggtggttgc ggtctggctc tgggttacca cacc                               34

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cggtggttgc ggtctgatgc tgggttacca cacc                               34

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggtggttgc ggtctgcagc tgggttacca cacc                               34

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 5
cggtggttgc ggtctgcgtc tgggttacca cacc                                34

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaggacggga aaccgtagta gataccgttc gg                                  32

<210> SEQ ID NO 7
<211> LENGTH: 1182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gaattcgtcc acccacttcg acgttatcgt tgttggtgct ggttccatgg gtatggctgc    60
tggttaccag ctggctaaac agggtgttaa aaccctgctg gttgacgctt cgacccgcc   120 gcacaccaac ggttcccacc acggtgacac ccgtatcatc cgtcacgctt acggtgaagg   180
tcgtgaatac gttccgctgg ctctgcgttc caggaactg tggtacgaac tggaaaaaga   240
aacccaccac aaaatcttca ccaaaaccgg tgttctggtt ttcggtccga aaggtgaatc   300
cgctttcgtt gctgaaacca tggaagctgc taaagaacac tccctgaccg ttgacctgct   360
ggaaggtgac gaaatcaaca aacgttggcc gggtatcacc gttccggaaa actacaacgc   420
tatcttcgaa ccgaactccg tgttctgtt ctccgaaaac tgcatccgtg cttaccgtga   480
actggctgaa gctcgtggtg ctaaagttct gacccacacc cgtgttgaag acttcgacat   540
ctccccggac tccgttaaaa tcgaaaccgc taacggttcc tacaccgctg acaaactgat   600
cgtttccatg ggtgcttgga actccaaact gctgtccaaa ctgaacctgg acatcccgct   660
gcagccgtac cgtcaggttg ttggtttctt cgaatccgac gaatccaaat actccaacga   720
catcgacttc ccaggtttca tggttgaagt tccgaacggt atctactacg gtttcccgtc   780
cttcggtggt tgcggtctgc gtctgggtta ccacaccttc ggtcagaaaa tcgacccgga   840
caccatcaac cgtgagttcg tgtttaccc ggaagacgaa tccaacctgc gtgcttcct    900 ggaagaatac atgccgggtg ctaacggtga actgaaacgt ggtgctgttt gcatgtacac   960 caaaacctg acgaacact tcatcatcga cctgcacccg gaacactcca acgttgttat   1020
cgctgctggt ttctccggtc acggtttcaa attctcctcc ggtgttggtg aagttctgtc   1080
ccagctggct ctgaccggta aaccgaaca cgacatctcc atcttctcca tcaaccgtcc   1140
ggctctgaaa gaatccctgc agaaaaccac catctgaagc tt                     1182

<210> SEQ ID NO 8
<211> LENGTH: 1547
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
cgggatccga tgaacctgga aaaattcgtt gacgaactgc cgatcccgga agttgctaaa      60
ccggttaaaa aaaacccgaa acagacctac tacgaaatcg ctatggaaga agttttcctg     120
aaagttcacc gtgacctgcc gccgaccaaa ctgtggacct acaacggttc cctgccgggt     180
ccgaccatcc acgctaaccg taacgaaaaa gttaaagtta aatggatgaa caaactgccg     240
ctgaaacact tcctgccggt tgaccacacc atccacgaag gtcaccacga cgaaccggaa     300
gttaaaaccg ttgttcacct gcacggtggt gttaccccgg cttcctccga cggttacccg     360
gaggcttggt tctcccgtga cttcgaagct accggtccgt tcttcgaacg tgaagtttac     420
gaatacccga accaccagca ggcttgcacc ctgtggtacc acgaccacgc tatggctctg     480
acccgtctga cgtttacgc tggtctggct ggtttctacc tgatctccga cgctttcgaa      540
aaatccctgg aactgccgaa aggtgaatac gacatcccgc tgatgatcat ggaccgtacc     600
ttccaggaag acggtgctct gttctacccg tcccgtccga caacaccccc ggaagactcc     660
gacatcccgg acccgtccat cgttccgttc ttctgcggtg aaaccatcct ggttaacggt     720
aaagtttggc cgtacctgga agttgaaccg cgtaaatacc gtttccgtat cctgaacgct     780
tccaacaccc gtacctacga actgcacctg gacaacgacg ctaccatcct gcagatcggt     840
tccgacggtg gtttcctgcc gcgtccggtt caccaccagt ccttctccat cgctccggct     900
gaacgtttcg acgttatcat cgacttctcc gcttacgaaa acaaaaccat caccctgaaa     960
aacaaagctg gttgcggtca ggaagttaac ccggaaaccg acgctaacat catgcagttc    1020
aaagttaccc gtccgctgaa aggtcgtgct ccgaaaaccc tgcgtccgat cttcaaaccg    1080
ctgccgccgc tgcgtccgtg ccgtgctgac aaagaacgta ccctgaccct gaccggtacc    1140
caggacaaat acggtcgtcc gatcctgctg ctggacaacc agttctggaa cgacccggtt    1200
accgaaaacc cgcgtctggg ttccgttgaa gtttggtcca tcgttaaccc gacccgtggt    1260 acccaccccga tccacctgca cctggttcag ttccgtgtta tcgaccgtcg tccgttcgac    1320
accgaagttt accagtccac cggtgacatc gtttacaccg gtccgaacga agctccgccg    1380
ctgcacgaac agggttacaa agacaccatc caggctcacg ctggtgaagt tatccgtatc    1440
atcgctcgtt tcgttccgta ctccggtcgt tacgtttggc actgccacat cctggaacac    1500
gaagactacg acatgatgcg tccgatggac atcatccagg tcgacaa                  1547
```

<210> SEQ ID NO 9
<211> LENGTH: 1748
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
ggatccaaca acatgtccag attcccatct attttcactg ctgttttgtt cgctgcttct      60
tctgctttgg ctgctccagt taacactact actgaaagag agaagagaga agctcaaatt     120
gatatctctc cacaatacccc aatgttcact gttccattgc caattccacc agttaagcaa     180
ccaagattga ctgttactaa cccagttaac ggtcaagaaa tttggtacta cgaagttgaa     240
attaagccat tcactcacca agtttacccca gacttgggtt ctgctgactt ggttggttac     300
gacggtatgt ctccaggtcc aactttccaa gttccaagag gtgttgaaac tgttgttaga     360
ttcattaaca acgctgaagc tccaaactct gttcacttgc acggtctttt ctccagagct     420
gctttcgacg gttgggctga agacattact gaaccaggtt ctttcaagga ctactactac     480
```

```
ccaaacagac aatctgctag aactttgtgg tatcacgacc acgctatgca cattactgct    540
gaaaacgctt acagaggtca agctggtttg tacatgttga ctgacccagc tgaagacgct    600
ttgaacttgc catctggtta cggtgaattt gacattccaa tgattttgac ttctaagcaa    660
tacactgcta acggtaactt ggttactact aacggtgaat tgaactcttt ctggggtgac    720
gttattcacg ttaacggtca accatggcca ttcaagaacg ttgaaccaag aaagtacaga    780
ttcagattct ggacgctgc tgtttccaga tctttcggtt tgtacttcgc tgacactgac    840
gctattgaca ctagattgcc attcaaggtt attgcttctg actctggttt gttggaacac    900
ccagctgaca cttctttgtt gtacatttct atggctgaaa gatacgaagt tgttttcgac    960
ttctctgact acgctggtaa gactattgaa ttgagaaact ggggtggttc tattggtggt   1020
attggtactg acactgacta cgacaacact gacaaggtta tgagattcgt tgttgctgac   1080
gacactactc aaccagacac ttctgttgtt ccagctaact gagagacgt tccattccca    1140 tctccaacta ctaacactcc aagacaattc agattcggta gaactggtcc aacttggact   1200
attaacggtg ttgctttcgc tgacgttcaa aacagattgt tggctaacgt tccagttggt   1260
actgttgaaa gatgggaatt gattaacgct ggtaacggtt ggactcaccc aattcacatt   1320
cacttggttg acttcaaggt tatttccaga acttctggta caacgctag aactgttatg   1380 ccatacgaat ctggtttgaa ggacgttgtt tggttgggta agagaaaac tgttgttgtt   1440 gaagctcact acgctccatt cccaggtgtt tacatgttcc actgtcacaa cttgattcac   1500
gaagaccacg acatgatggc tgctttcaac gctactgttt tgccagacta cggttacaac   1560
gctactgttt tcgttgaccc aatggaagaa ttgtggcaag ctagaccata cgaattgggt   1620
gaatttcaag ctcaatctgg tcaattctct gttcaagctg ttactgaaag aatccaaact   1680
atggctgaat acagaccata cgctgctgct gaccatcatc accatcacca ttgagcggcc   1740
gcctgcag                                                            1748
```

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gctagaactt tgtggtatgc tgacgctgct atgcacatta ctgctg                    46

<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gctagaactt tgtggtatta cgactacgct atgcacatta ctgctg                    46

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gctagaactt tgtggtatta cgacgctgct atgcacatta ctgctg         46

<210> SEQ ID NO 13
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gctagaactt tgtggtattt tgactttgct atgcacatta ctgctg         46

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gctagaactt tgtggtattc tgactctgct atgcacatta ctgctg         46

<210> SEQ ID NO 15
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gctagaactt tgtggtataa ggacaaggct atgcacatta ctgctg         46

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agattgtctg tttgggtagt agtagtcctt gaaagaacc         39

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccaggtgttt acatgttcta ctgtgctaac ttgattcacg aagacc         46

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccaggtgttt acatgttctt tgttttaac ttgattcacg aagacc        46

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccaggtgttt acatgttcgc ttgtgctaac ttgattcacg aagacc        46

<210> SEQ ID NO 20
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccaggtgttt acatgttctc ttgttacaac ttgattcacg aagacc        46

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gaatggagcg tagtgagctt caacaacaac agtttctctt ctacc        45

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gcttgcaccc tgtggtacgc tgacgctgct atggctctga cccgtctg        48

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcttgcaccc tgtggtacta cgactacgct atggctctga cccgtctg        48

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcttgcaccc tgtggtacta cgacgctgct atggctctga cccgtctg            48

<210> SEQ ID NO 25
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcttgcaccc tgtggtactt cgacttcgct atggctctga cccgtctg            48

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcttgcaccc tgtggtactc cgactccgct atggctctga cccgtctg            48

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcttgcaccc tgtggtacaa agacaaagct atggctctga cccgtctg            48

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctgctggtgg ttcgggtatt cg                                        22

<210> SEQ ID NO 29
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cgtactccgg tcgttacgtt tggtactgcg ctatcctgga acacgaagac tacg      54

<210> SEQ ID NO 30
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
cgtactccgg tcgttacgtt tggttctgct tcatcctgga acacgaagac tacg            54

<210> SEQ ID NO 31
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgtactccgg tcgttacgtt tgggcttgcg ctatcctgga acacgaagac tacg            54

<210> SEQ ID NO 32
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgtactccgg tcgttacgtt tggtcctgct acatcctgga acacgaagac tacg            54

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gaacgaaacg agcgatgata cgg                                              23

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 34

His His His His His His
1               5
```